(12) United States Patent
Akingba et al.

(10) Patent No.: US 10,184,851 B2
(45) Date of Patent: Jan. 22, 2019

(54) SUPERSENSITIVE LINEAR PRESSURE TRANSDUCER

(71) Applicants: Indiana University Research and Technology Corporation, Indianapolis, IN (US); Purdue Research Foundation, West Lafayette, IN (US)

(72) Inventors: A. George Akingba, Carmel, IN (US); Jason V. Clark, West Lafayette, IN (US)

(73) Assignees: Indiana University Research and Technology Corporation, Indianapolis, IN (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/198,452

(22) Filed: Jun. 30, 2016

(65) Prior Publication Data

US 2017/0059433 A1   Mar. 2, 2017

Related U.S. Application Data

(63) Continuation of application No. 13/807,431, filed as application No. PCT/US2011/042713 on Jun. 30, 2011, now Pat. No. 9,408,555.

(Continued)

(51) Int. Cl.
*G01L 7/08*      (2006.01)
*G01L 9/12*      (2006.01)
(Continued)

(52) U.S. Cl.
CPC .............. *G01L 9/0072* (2013.01); *A61B 5/03* (2013.01); *A61B 5/08* (2013.01); *A61B 5/113* (2013.01);
(Continued)

(58) Field of Classification Search
CPC ............................... G01L 9/0072; G01L 7/08
See application file for complete search history.

(56) References Cited

U.S. PATENT DOCUMENTS 5,025,346 A    6/1991  Tang
5,113,868 A *  5/1992  Wise .................. A61B 5/02158
                                                           600/486

(Continued)

FOREIGN PATENT DOCUMENTS

EP    1835294 A1 *  9/2007  ........... B81B 3/0062
EP    2520333 A1 * 11/2012  ........... A61N 1/3785
(Continued)

OTHER PUBLICATIONS

WIPO, International Preliminary Report on Patentability, dated Jan. 17, 2013, 6 pages Jan. 17, 2013.
(Continued)

*Primary Examiner* — Lisa Caputo
*Assistant Examiner* — Herbert K Roberts
(74) *Attorney, Agent, or Firm* — Faegre Baker Daniels LLP

(57) ABSTRACT

Apparatus and methods for a MEMS-fabricated variable capacitor. In one embodiment the capacitor is a comb drive comprising a plurality of plates interdigitated with a corresponding blades. As the plates move relative to the blades, the capacitance of the sensor changes. The capacitor is sufficiently sensitive to measure respiratory pressure in an animal.

30 Claims, 23 Drawing Sheets

Related U.S. Application Data

(60) Provisional application No. 61/360,291, filed on Jun. 30, 2010.

(51) Int. Cl.
| | | |
|---|---|---|
| *A61B 5/0215* | (2006.01) | |
| *G01L 9/00* | (2006.01) | |
| *A61B 5/03* | (2006.01) | |
| *A61B 5/08* | (2006.01) | |
| *A61B 5/113* | (2006.01) | |
| *A61B 5/00* | (2006.01) | |
| *A61M 16/00* | (2006.01) | |
| *H04R 19/00* | (2006.01) | |

(52) U.S. Cl.
CPC ............ *A61B 5/6867* (2013.01); *A61B 5/686* (2013.01); *A61B 5/6846* (2013.01); *A61B 2562/028* (2013.01); *A61B 2562/0247* (2013.01); *A61M 2016/0021* (2013.01); *A61M 2016/0027* (2013.01); *A61M 2205/04* (2013.01); *A61M 2205/332* (2013.01); *A61M 2205/3317* (2013.01); *H04R 19/00* (2013.01); *H04R 2201/003* (2013.01)

(56) References Cited

U.S. PATENT DOCUMENTS

| | | | |
|---|---|---|---|
| 5,445,006 A | | 8/1995 | Allen et al. |
| 5,610,335 A | | 3/1997 | Shaw et al. |
| 5,703,754 A | | 12/1997 | Hinze |
| 6,012,336 A | * | 1/2000 | Eaton .................. B81C 1/00246 73/754 |
| 6,073,484 A | | 6/2000 | Miller et al. |
| 6,189,374 B1 | | 2/2001 | Adderton et al. |
| 6,311,563 B1 | | 11/2001 | Ishikura |
| 6,505,516 B1 | | 1/2003 | Frick et al. |
| 6,571,628 B1 | | 6/2003 | Miao et al. |
| 6,584,864 B2 | | 7/2003 | Greenwood |
| 6,780,664 B1 | | 8/2004 | Goruganthu et al. |
| 7,111,504 B2 | | 9/2006 | Blumbert et al. |
| 7,253,616 B2 | | 8/2007 | Bolle et al. |
| 7,287,415 B2 | | 10/2007 | Borwick, III et al. |
| 7,296,478 B2 | | 11/2007 | Fortin et al. |
| 7,331,236 B2 | | 2/2008 | Smith et al. |
| 7,600,428 B2 | | 10/2009 | Robert et al. |
| 7,721,587 B2 | | 5/2010 | Clark |
| 7,737,514 B1 | | 6/2010 | Fu |
| 7,900,518 B2 | | 3/2011 | Tai et al. |
| 8,104,358 B1 | * | 1/2012 | Jia ......................... G01L 9/0072 73/780 |
| 8,966,990 B2 | | 3/2015 | Clark |
| 2002/0127760 A1 | * | 9/2002 | Yeh ...................... B81C 1/00182 438/50 |
| 2004/0027029 A1 | | 2/2004 | Borwick, III et al. |
| 2004/0231420 A1 | * | 11/2004 | Xie ........................ B81B 3/0062 73/514.32 |
| 2005/0068989 A1 | | 3/2005 | Herbert et al. |
| 2005/0081363 A1 | | 4/2005 | Malshe et al. |
| 2005/0241394 A1 | | 11/2005 | Clark |
| 2005/0248340 A1 | | 11/2005 | Berkcan et al. |
| 2006/0082543 A1 | | 4/2006 | Van Lydegraf et al. |
| 2006/0137453 A1 | | 6/2006 | Wu et al. |
| 2007/0044545 A1 | | 3/2007 | Beyder et al. |
| 2007/0085533 A1 | | 4/2007 | Bolle et al. |
| 2008/0058632 A1 | | 3/2008 | Tai et al. |
| 2011/0000303 A1 | | 1/2011 | Fortner et al. |
| 2012/0017693 A1 | * | 1/2012 | Robert .................. B81B 3/0021 73/753 |
| 2012/0204643 A1 | * | 8/2012 | Clark ...................... H01G 5/16 73/514.32 |

FOREIGN PATENT DOCUMENTS

| | | |
|---|---|---|
| WO | 9506236 | 3/1995 |
| WO | 9617430 | 6/1996 |
| WO | 2006039072 | 4/2006 |

OTHER PUBLICATIONS

KIPO, Search Report and Written Opinion, dated Feb. 24, 2012, 9 pages Feb. 24, 2012.
PCT/US2011/042713, WIPO, International Preliminary Report on Patentability, dated Jan. 17, 2013, 6 pages Jan. 17, 2013.
PCT/US2011/042713, KIPO, Search Report and Written Opinion, dated Feb. 24, 2012, 9 pages Feb. 24, 2012.
U.S. Appl. No. 13/807,431, First Office Action dated Dec. 31, 2014, 28 pages.
U.S. Appl. No. 13/807,431, Applicant Response filed Jun. 30, 2015, 16 pages.
U.S. Appl. No. 13/807,431, Final Office Action dated Oct. 7, 2015, 24 pages.
U.S. Appl. No. 13/807,431, Applicant Response to Final OA dated Mar. 31, 2016, 5 pages.
NOA dated Apr. 19, 2016, 5 pages.

* cited by examiner

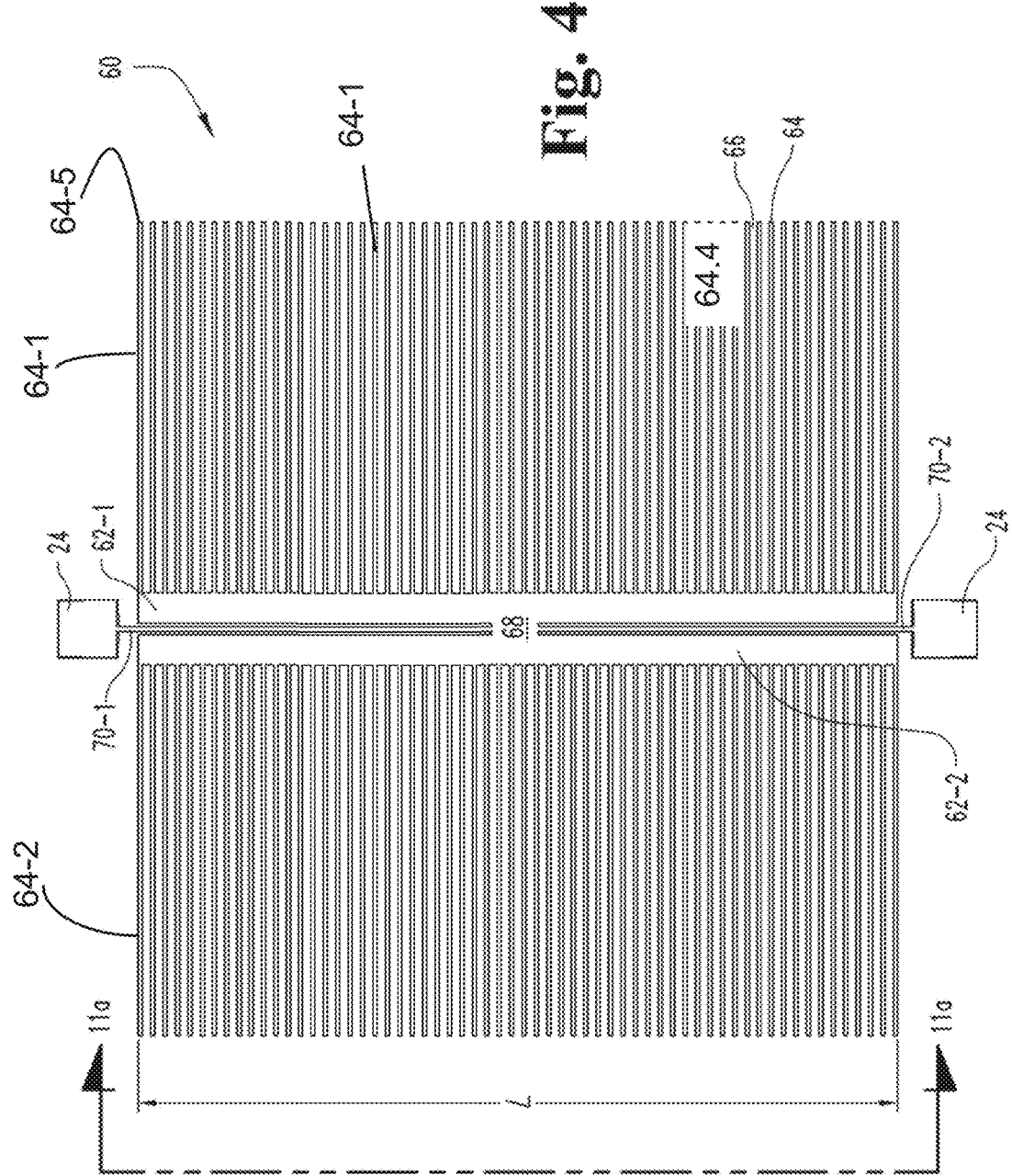

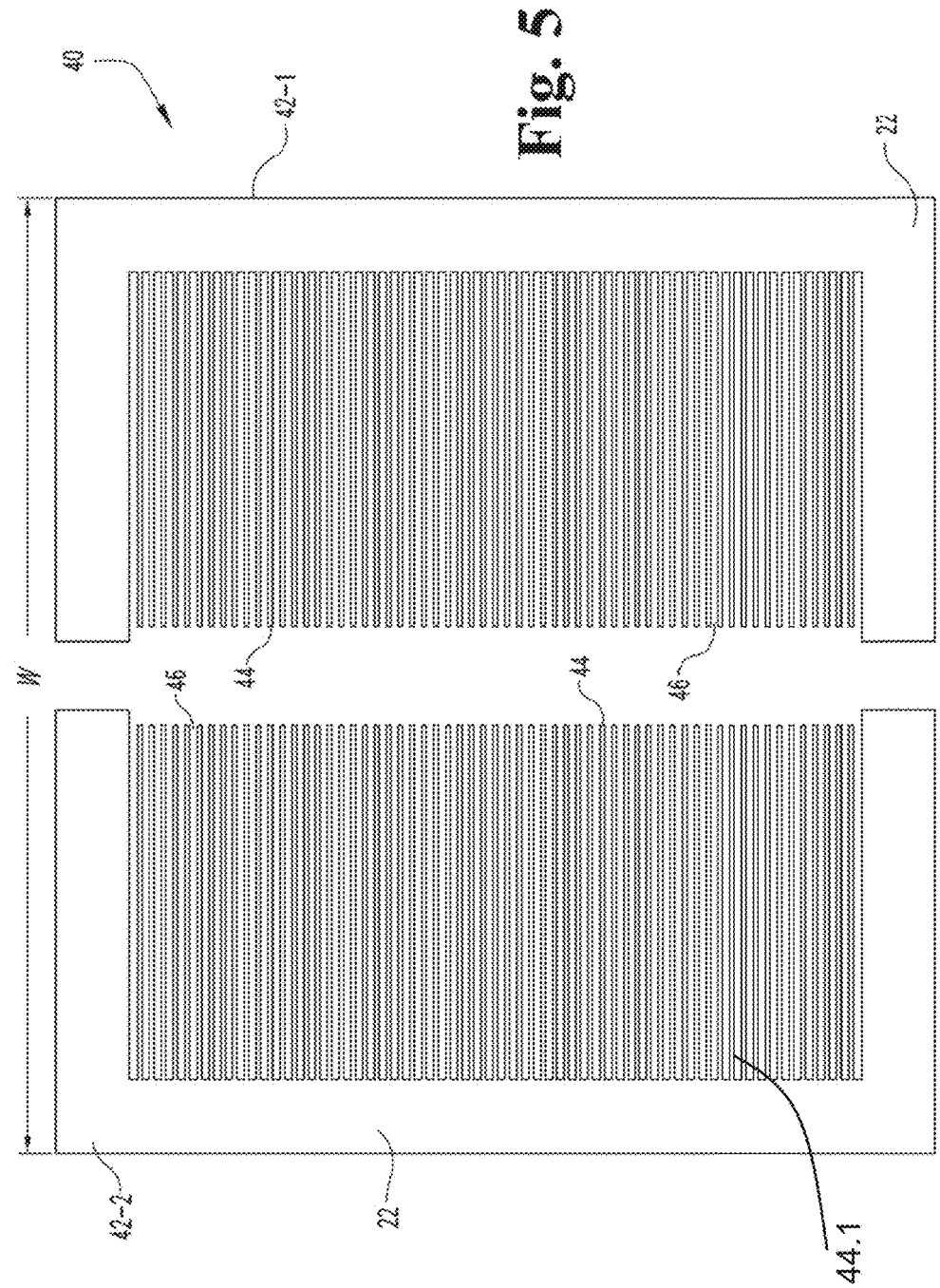

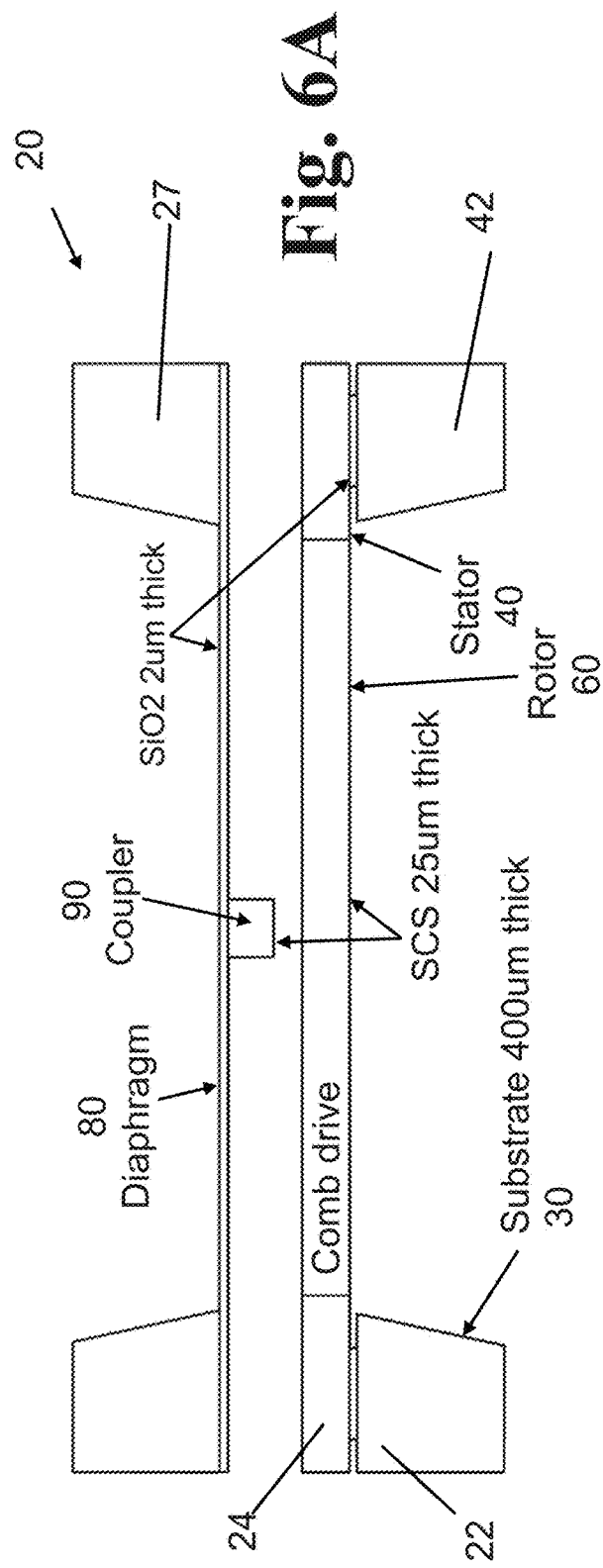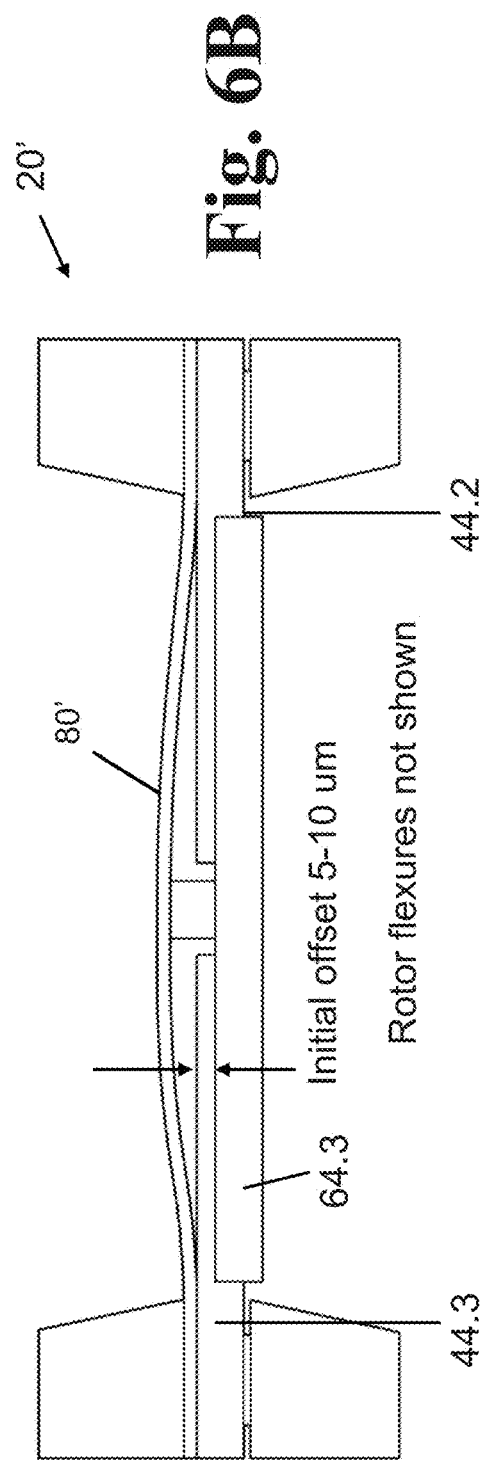

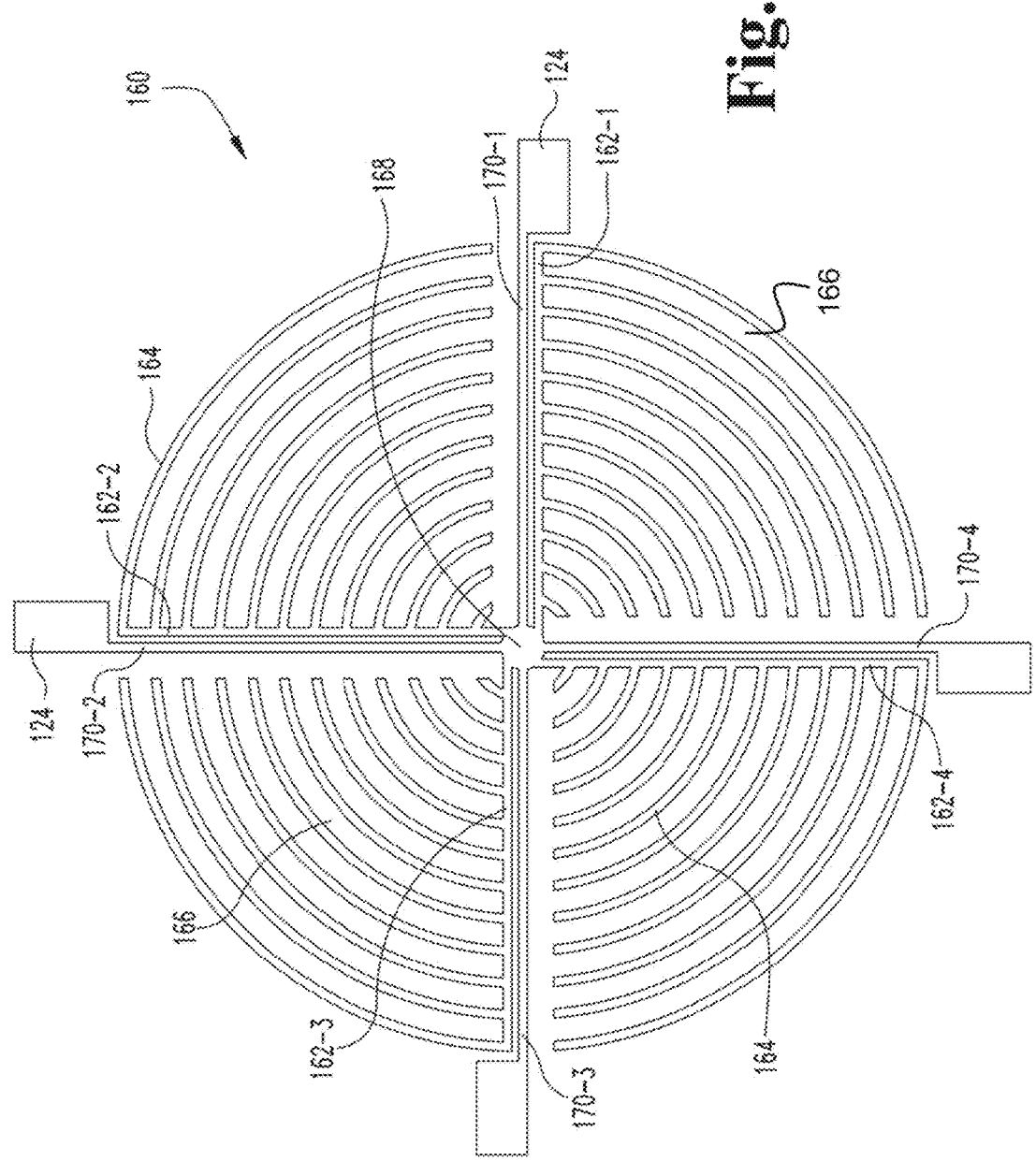

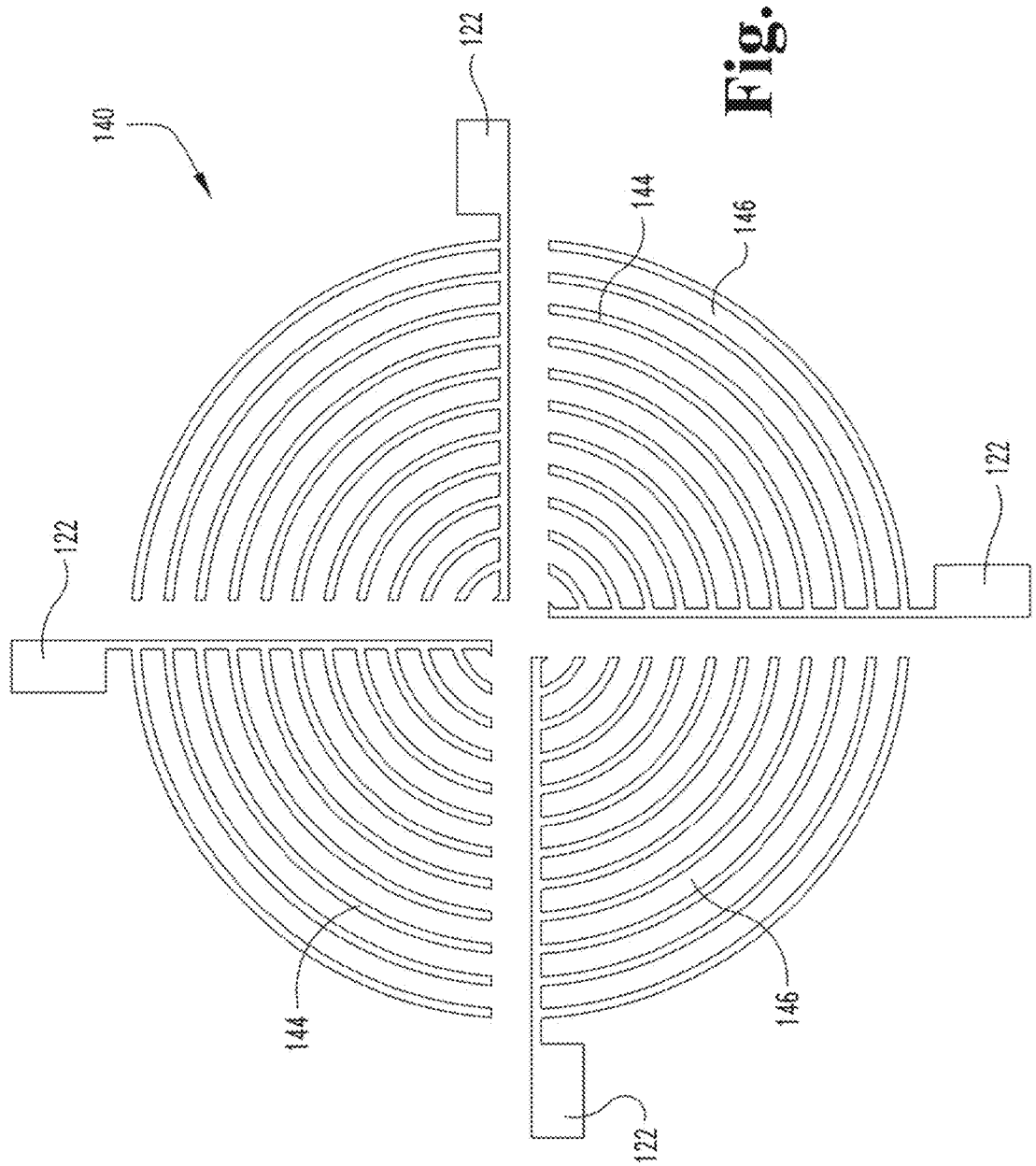

SUPERSENSITIVE LINEAR PRESSURE TRANSDUCER

CROSS REFERENCE TO RELATED APPLICATION

This application is a continuation of U.S. Ser. No. 13/807,431, filed Dec. 28, 2012, which was the U.S. National Stage of International Application No. PCT/US2011/042713, filed Jun. 30, 2011, which claims the benefit of U.S. Provisional Patent Application No. 61/360,291, filed Jun. 30, 2010, the entireties of which are hereby incorporated herein by reference. Any disclaimer that may have occurred during the prosecution of the above-referenced applications is hereby expressly rescinded.

FIELD OF THE INVENTION

Various aspects of the present invention pertain to pressure transducers and, in particular, to pressure transducers implantable within an animal airway, and to transducers including comb capacitors.

BACKGROUND OF THE INVENTION

Long-term mechanical ventilation incurs substantial morbidity, mortality, and costs (1% to 1.5% of the United States GDP). Because both premature and delayed ventilator weaning can cause harm, a weaning protocol that is both expeditious and safe is helpful. For these reasons, physicians are interested in an evidence-based approach to weaning from mechanical ventilation. One aspect of some embodiments of the present invention is to develop an implantable microsensor to measure pressure in the pleural space. This would permit quantification of, currently unmeasured elements of respiratory mechanics that can then be incorporated into a clinical management scheme to improve the outcome of patients on ventilator support. During ventilator support, direct pleural pressure monitoring combined with other available parameters will improve understanding of the relationship between a patient's inspiratory effort, lung compliance, airway resistance, and work of breathing. This information will be useful in narrowing the differential diagnosis and grading the severity of respiratory distress, thereby enabling the clinician to tailor ventilator settings to the individual patient.

Historically, the technique of mechanical ventilation has grown from being used temporarily during surgical procedures to being a mainstay of life support for the critically ill patient. It has been estimated that ICU care accounts for 20% to 34% of all hospital costs, 7% to 8% of total healthcare costs and 1% to 1.5% of the United States gross domestic product. Patients requiring long-term mechanical ventilation in the ICU consume approximately 50% of ICU resources, despite the fact that they represent less than 10% of all ICU patients. Short-term ventilation (<48-hrs) is associated with excellent survival and a relatively short (i.e. inexpensive) hospital stay. However, it is attainable in less than 25% of all ventilated patients, and accounts for a very small percentage of total ventilator days.

On the other hand, studies show that 11-40% of ventilated patients admitted to the medical ICU required more than 1 week of mechanical ventilator support, and only 40-50% of these patients were eventually weaned during the monitored period of these studies. The weaning process may require weeks to months of care, thus consuming enormous ICU resources. A ventilator-dependent ICU patient has an estimated cost that is eight times that of a patient on a general medical/surgical floor. Crude estimates put the nationwide cost of mechanical ventilation for the year 1995 in the range of $30 billion, exclusive of physician costs and the costs associated with long-term post-ventilator care.

Premature extubation followed by reintubation is associated with a six-fold increase in mortality compared with patients who can tolerate extubation. On the other hand, the costs associated with prolonged mechanical ventilation are not trivial. A European survey of practices related to mechanical ventilation indicated that approximately 42% of a patient's time on a ventilator is spent in the process of weaning.

The traditional measurements of respiratory mechanics that are currently used clinically to predict weaning success are hampered by false positives and false negatives. This makes the physician's judgment the determining factor. For example, one of the predictive indices, the RSBI (rapid shallow breathing index) has a sensitivity of 65-96% and a specificity of 0-73%. The reason behind the suboptimal performance of these predictors is based on poor understanding of the direct "inspiratory effort" (i.e. intrapleural pressure). The inspiratory effort expended by patients with acute respiratory failure ranges from four to six times the normal value. If this level of effort is sustained indefinitely in critically ill patients, they are prone to develop inspiratory-muscle fatigue. With careful selection of MV settings, inspiratory effort (IE) can be reduced to the normal range.

However, eliminating IE entirely is not desirable because it causes deconditioning and atrophy of the respiratory muscles. Presently with the available parameters, it is difficult to precisely and directly measure IE (i.e. intrapleural pressure). Therefore, physicians cannot actively pursue a target IE in a given ventilated patient. In addition, to trigger the ventilator, the patient's IE first has to result in a negative airway pressure. The negative intrapleural pressure counters the lung's elastic recoil and airway conduit resistance in order to generate a negative airway pressure that is less than the ambient pressure. This airway pressure is measured by the ventilator, and should reach a set sensitivity target to trigger the ventilator to provide a full breath. If the patient's effort is insufficient to trigger the ventilator, then that effort is "wasted". The consequences of wasted IE's are not fully known, but they add an unnecessary burden in patients whose inspiratory muscles are already under stress.

From a pathophysiological standpoint, continuous direct intrapleural pressure monitoring by an implantable microsensor integrated with other non-invasive respiratory measurements (tidal volume and flow rate) will allow calculation of the compliance, airway resistance, and work of breathing in mechanically ventilated patients. Knowledge of the compliance or airway resistance will assist physicians in narrowing their differential diagnosis, while measurements of spontaneous work of breathing will allow for a better index of lung disease severity and weaning potential.

What is needed are inventive apparatus and methods for improved measurement of respiratory pressures, and also for variable capacitors with increased resolution. Various embodiments of the present invention achieve these improvements in novel and nonobvious ways.

SUMMARY OF THE INVENTION

One aspect of some embodiments pertains to the fabrication of an implantable capacitive pressure sensor using microelectro-mechanical systems (MEMS) technology.

One aspect of the present invention pertains to a variable capacitor. One embodiment further includes a stator including a plurality of electrically conductive plates each spaced apart from one another, each of said plates being in a first common electrical communication. Another embodiment includes a rotor including a central hub and first and second arms extending in cantilever manner from opposite sides of said hub, a first plurality of electrically conductive blades being coupled to said first arm and a second plurality of electrically conductive blades being coupled to said second arm, each of said first plurality and said second plurality of blades being in a second common electrical communication. In still further embodiments, the hub is suspended from said stator by first and second springs, such that each of said blades is received between plates, and the capacitance between the first electrical communication and the second electrical communication varies as said first and second springs bias the rotor to different positions relative to said stator.

Another aspect of the present invention pertains to a capacitor. One embodiment includes a stator having a width and including a plurality of electrically conductive plates each spaced apart from one another, each of said plates being in a first common electrical communication. Yet other embodiments include a rotor having a length and including a plurality of electrically conductive blades, said rotor being suspended relative to said stator such that each of said blades is received between plates, each of said blades being in a second common electrical communication. Still other embodiments include a means for biasing a rotor relative to said stator, said means flexibly coupling to a stator at a location about midway across the width, said means flexibly coupling to a rotor at a location about midway along the length.

Yet another aspect of the present invention pertains to a method for transducing air pressure. Some embodiments include providing a diaphragm, a stator including a plurality of electrically conductive plates, and a rotor movable relative to the stator and including a plurality of electrically conductive blades and interdigitating the blades and the plates. Other embodiments include coupling the diaphragm to the rotor such that the motion of the rotor is substantially unresponsive to movement of the diaphragm in any direction except one. Still further embodiments include applying a pressure differential across the diaphragm, deflecting the diaphragm by said applying, moving the blades relative to the plates by said deflecting; and changing the electrical capacitance of the rotor and stator by said moving.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 4 is a top plan view of the rotor of the sensor of FIG. 3.

FIG. 5 is a top plan view of the stator of the pressure sensor of FIG. 3.

FIG. 6A is a partial cross sectional, exploded view of portions of the sensor of FIG. 3.

FIG. 6B is a non-exploded view of the apparatus of FIG. 6A.

FIG. 15 is a top plan view of a rotor for a sensor according to one embodiment of the present invention.

FIG. 16 is a top plan view of a stator for a sensor according to one embodiment of the present invention, adapted and configured for the rotor of FIG. 15.

DESCRIPTION OF THE PREFERRED EMBODIMENT

Figure 1:
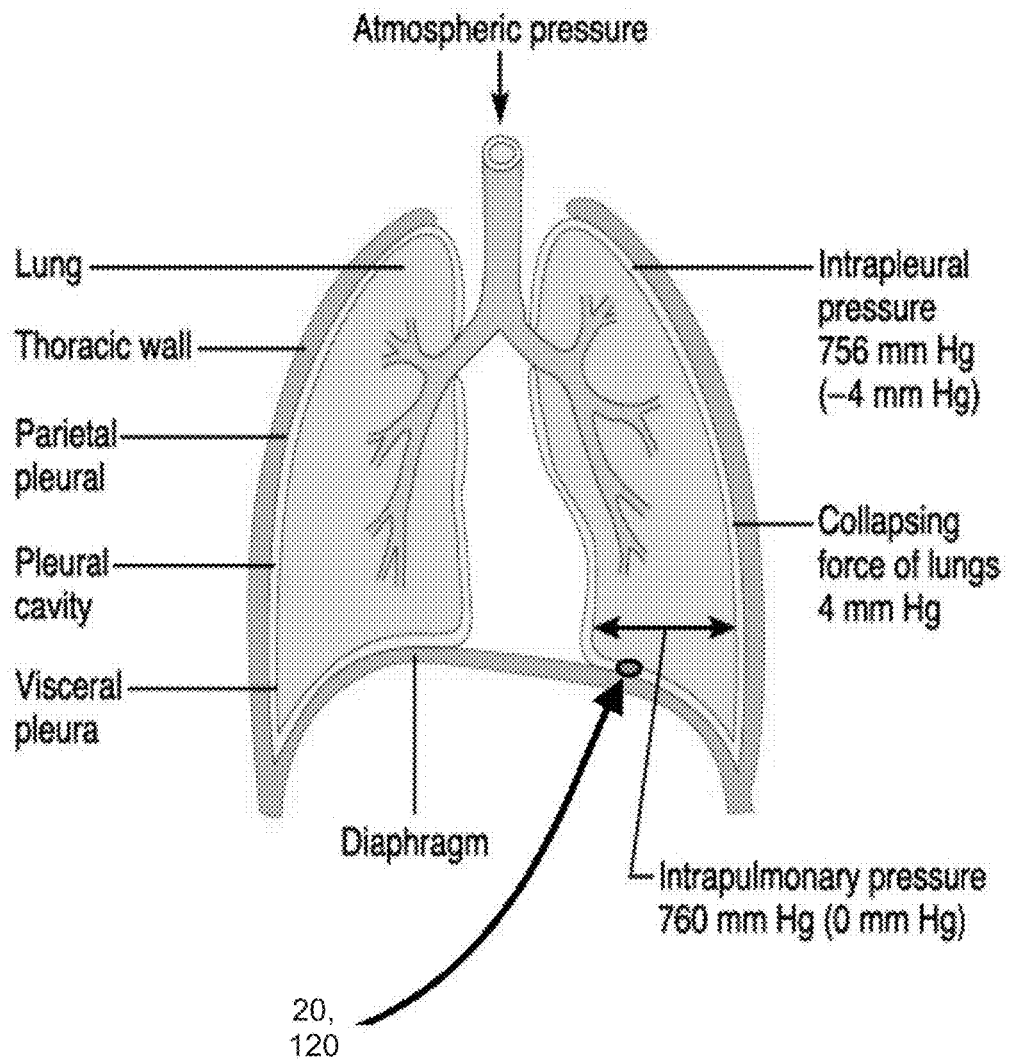
FIG. 1 is a schematic cross sectional representation of a portion of an animal respiratory system having an implanted pressure sensor according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

Various embodiments of the present invention pertain to a pressure sensor with sufficient sensitivity to detect small pressure changes, such as pressure changes during respiration of an animal. In some embodiments, the sensor is fabricated biocompatible materials, and with some portions of the sensor hermetically sealed off from the environment. However, yet other embodiments of the present invention pertain to pressure transducers suitable for use in industrial applications and cell phones.

Yet other embodiments of the present invention pertain to configurations of comb drives that exhibit relatively changes in capacitance as the comb rotor moves relative to the comb stator. Such novel variable capacitors can be used in any application in which it is desirable to change capacitance when a motion is imposed on an element of the capacitor. Applications for such a capacitor includes sensors for measurement of acceleration and strain.

Yet other embodiments of the present invention pertain to methods and apparatus for suspending one combed element within another combed element. It has been found that this suspension can be viable in a micromachined sensor. Several aspects improving the practicality of such a suspension include having a suspension system that has a first, lower stiffness in one direction, but second and higher stiffnesses in lateral directions, such that the suspended combed element preferably moves in a single direction. Yet another aspect of some embodiments is to use a suspension system that couples to the suspended element such that the mass distribution of the suspended element is symmetrical about one or two axes. Yet another aspect in some suspended elements is the imposition of loads on the suspended element by means that permits the imposition of a load in one dimension, but which cannot substantially transmit loads transverse to that direction, nor which can transmit moments or torques in any direction.

The lungs can be modeled as inflating/deflating balloons with the diaphragm and chest wall acting as mechanical bellows. Using this model the fundamental properties of the ventilation system [lung compliance (C), airway resistance (R), and inertance (I)] can be represented by the three-dimensional equivalent of Newton's equation of motion: $P(t)=(1/C)\cdot V(t)+R\cdot V'+I\cdot V''$. For spontaneous ventilation, $P(t)$ is the pleural pressure as a function of time, $V(t)$ is the tidal volume as a function of time, $V'$ and $V''$ are the tidal volume time derivatives, flow and acceleration respectively. The inertance, which measures the tendency of the ventilator system to resist changes in flow, is customarily insignificant. Since tidal volume and airflow measurements can be obtained invasively or non-invasively, then the addition of pleural pressure measurements makes the above differential equation solvable for lung compliance and airway resistance, which both have significance in differential diagnosis. From this same equation, it is possible to determine spontaneous work of breathing ($W_b$) which is the integral of pleural pressure (P) over a volume change (dV). Spontaneous work of breathing in a ventilated patient is an index of severity of lung disease. Based on simple pulmonary mechanics, the upper-limit ratio of intra-pleural pressure (0-7 mm Hg) to tidal volume (0-700 ml) is approximately 1 to 100, therefore the average slope of the pressure-volume curve ($\Delta P/\Delta V$) is 0.01 mmHg/ml. This means in order to accurately measure the work done ($W_b=\int P\cdot dV$) for 1 ml of volume change, the sensor should be capable of accurately determining a 0.01 mmHg change in pleural pressure, which is a higher resolution in the low-pressure range than is available using current pressure sensing technology.

Silicon micromachined capacitive pressure sensors are useful for pressure sensing because of their high precision, low temperature sensitivity, low power consumption, and relatively simple fabrication. A micromachined capacitive pressure sensor according to one embodiment utilizes comb-drive structures on a flexible diaphragm. This structural configuration results in a substantially linear transduction gradient, and high-aspect ratio structures lead to high capacitance values. A capacitive pressure sensor using comb-drives shows simulated device sensitivity in the micro-mmHg range and a linear slope within the pressure range of interest.

One embodiment of the present invention pertains to a minimally invasive approach to introduce a highly sensitive capacitive pressure sensor into the pleural space, such as in order to continuously monitor the inspiratory effort (i.e.

intrapleural pressure) generated by the respiratory musculature. Direct intrapleural pressure measurements are not currently included in the clinical assessment of the respiratory system, particularly because current pressure sensors do not have the sensitivity to evaluate the small pressure variations that occur in this location. In some applications, silicon micromachined capacitive pressure sensors are appealing for pressure sensing because of their precision, low temperature sensitivity, low power consumption, and relatively simple fabrication. Since the upper-limit ratio of pressure range (0-7 mmHg) to tidal volume range (0-700 ml) is approximately 1 to 100, then in order to accurately determine small changes in work of breathing, some embodiments of the present invention provide higher resolution in low-pressure measurements than is available using some current pressure sensing technology. some embodiment include a micromachined capacitive pressure sensor (20, 120) that varies the vertical overlapping area of interdigitated comb-fingers on a deflectable membrane for electro-mechanical transduction. some embodiments pertain to capacitive pressure sensor having an accuracy approaching ±0.01% FS. Further still, some embodiments include such accuracy in a small, implantable, biocompatible, hermetically sealed package.

Transpulmonary pressure (airway pressure–intrapleural pressure), is the resultant force that causes the alveoli to expand during spontaneous breathing. Without direct pleural pressure monitoring it is difficult to assess the spontaneous work of breathing performed by the patient or the relative contribution of abnormalities in the lung to a change in compliance or airway resistance. The first techniques developed for measuring pleural pressure used a needle in the pleural space connected to a pressure transducer. This procedure involves a certain amount of danger, especially if measurements are to be made during rapid breathing or maximal expiratory flow tests. Later it was found that esophageal pressure could be used to estimate changes in pleural pressure, thus providing a less invasive means of studying work of breathing. Unfortunately, physicians have not universally adopted esophageal pressure (Pes) estimates of pleural pressure. Reproducibility of measurements has been an issue as attention to equipment setup is helpful to avoid inaccurate results. Other limitations of some approaches include repeated measurements of balloon volume while obtaining pressure data, erroneous estimates above 32 Hz, fluctuations in Pes with changing patient position, and variability with absolute pleural pressure at low lung volumes.

Some embodiments of the present invention pertain to an implantable pressure sensor that allows measurement pleural pressure with improved selectivity and sensitivity. Some embodiments can continuously monitora patient's direct spontaneous inspiratory effort. This measurement is useful in better ascertaining the elements of the respiratory mechanical system (compliance, resistance, inertance) and the work of breathing. Based on this information, the physician can better characterize the pathophysiology of a patient's respiratory disorder, optimize ventilator settings, and determine the appropriate time for discontinuation of ventilator support. In addition, some embodiments of the pressure sensor may also be used as a more sensitive triggering device during MV. This can reduce the rate of wasted IE's made by some patients.

Some features of a pressure sensor according to some embodiments include a comb drive. Comb drives, as opposed to conventional gap-closing sensors, are linear, while gap-closing sensors are nonlinear in displacement which complicates characterization and data acquisition. In addition, comb drives allow for larger displacements, while the gap-closers typically have a small displacement before they become unstable. The large displacement of a pressure sensor according to some embodiments enables it to be more precise than conventional pressure sensors. Another feature of some embodiments is an initial offset in the range of the comb drive which allows the device to always operate within the linear operating range. Data showing some of the benefits of this offset is given in FIG. 12.

Figure 2A:
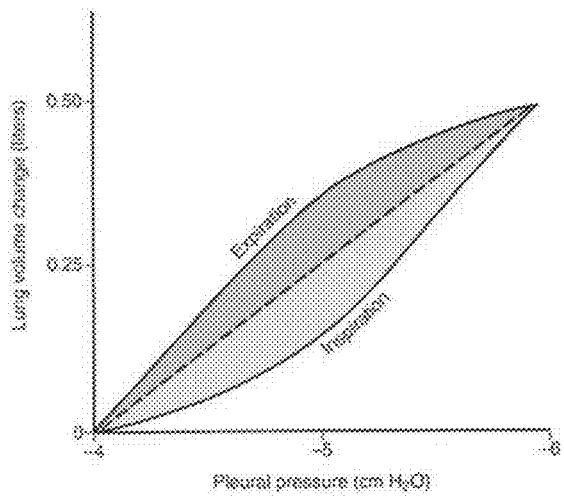
FIG. 2A is a graphical representation of lung volume change as a function of pleural pressure.
Figure 2B:
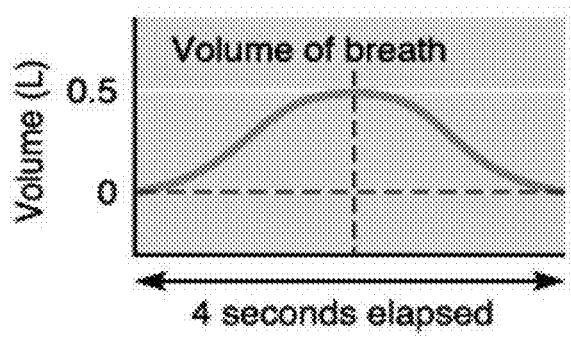
FIG. 2B is a graphical representation of lung volume as a function of time.
Figure 2C:
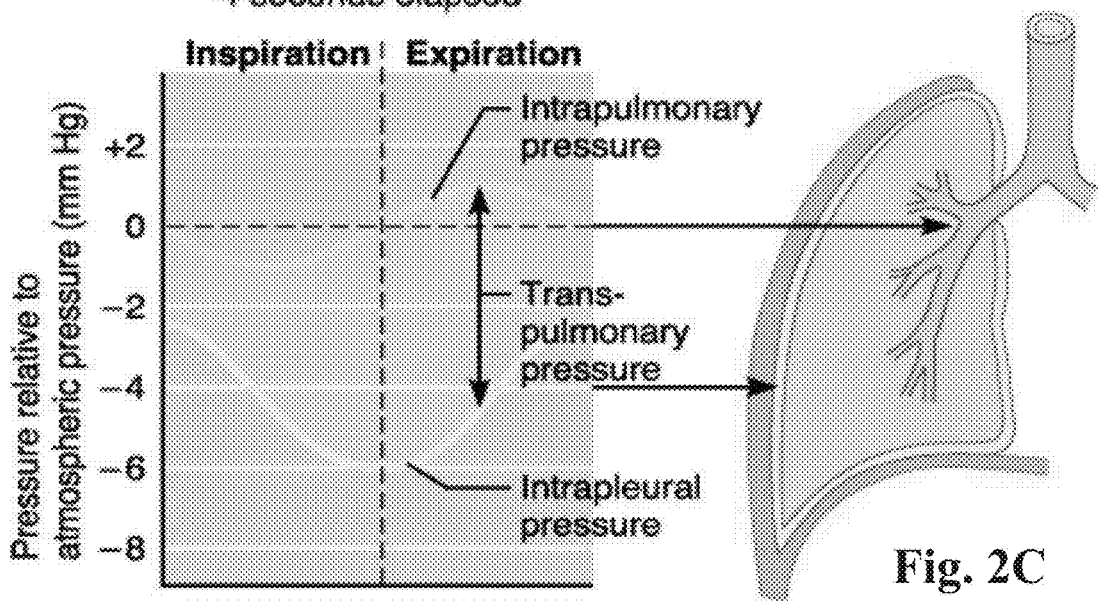
FIG. 2C is a graphical representation of lung gauge pressure as a function of time.

FIG. 1 is a schematic representation of animal lungs that are monitored with a pressure sensor according to one embodiment of the present invention. FIG. 1 shows the sensor located so as to measure intrapleural pressure. FIGS. 2A, 2B, and 2C provide further background of the pressure, volume, and timing characteristics representative of a human respiratory system. it is understood that the pressure sensors 20 and 120 shown and described herein are suitable, in some embodiments, for use in an animal body, the sensors being fabricated from biocompatible materials. Further, the variable capacitors used in these sensors can be hermetically sealed to further enhance their biocompatibility. Although what will be shown and described are pressure sensors adapted and configured for use in an animal respiratory system, it is understood that pressure sensors according to various embodiments of the present invention are not so limited. For example, the present invention contemplates the use of such biocompatible pressure sensors in the measurement of other pressures, including intraocular and vascular pressures.

Further, it is understood that the variable capacitors shown and described herein have applications beyond the sensing of air pressure. Various embodiments of the present invention pertain to capacitors having a capacitance that changes as a result of movement of one electrode (represented in some embodiments by a rotor) relative to another electrode (represented in some embodiments by a stator). Such variable capacitors can be used in any application in which it is desired to transducer a physical phenomenon to a corresponding electrical charge, especially when the physical phenomenon can be used to change the position of one electrode (such as the rotor) relative to the other electrode (such as the stator). As another example, variable capacitors shown herein are applicable for the measurement of vibration, such as in those cases where the housing of the capacitor is attached to a moving object that vibrates. In another embodiment, a variable capacitor can be used to transducer sound such as from a human voice to an electrical signal, as is useful with a cell phone or microphone.

Figure 3:
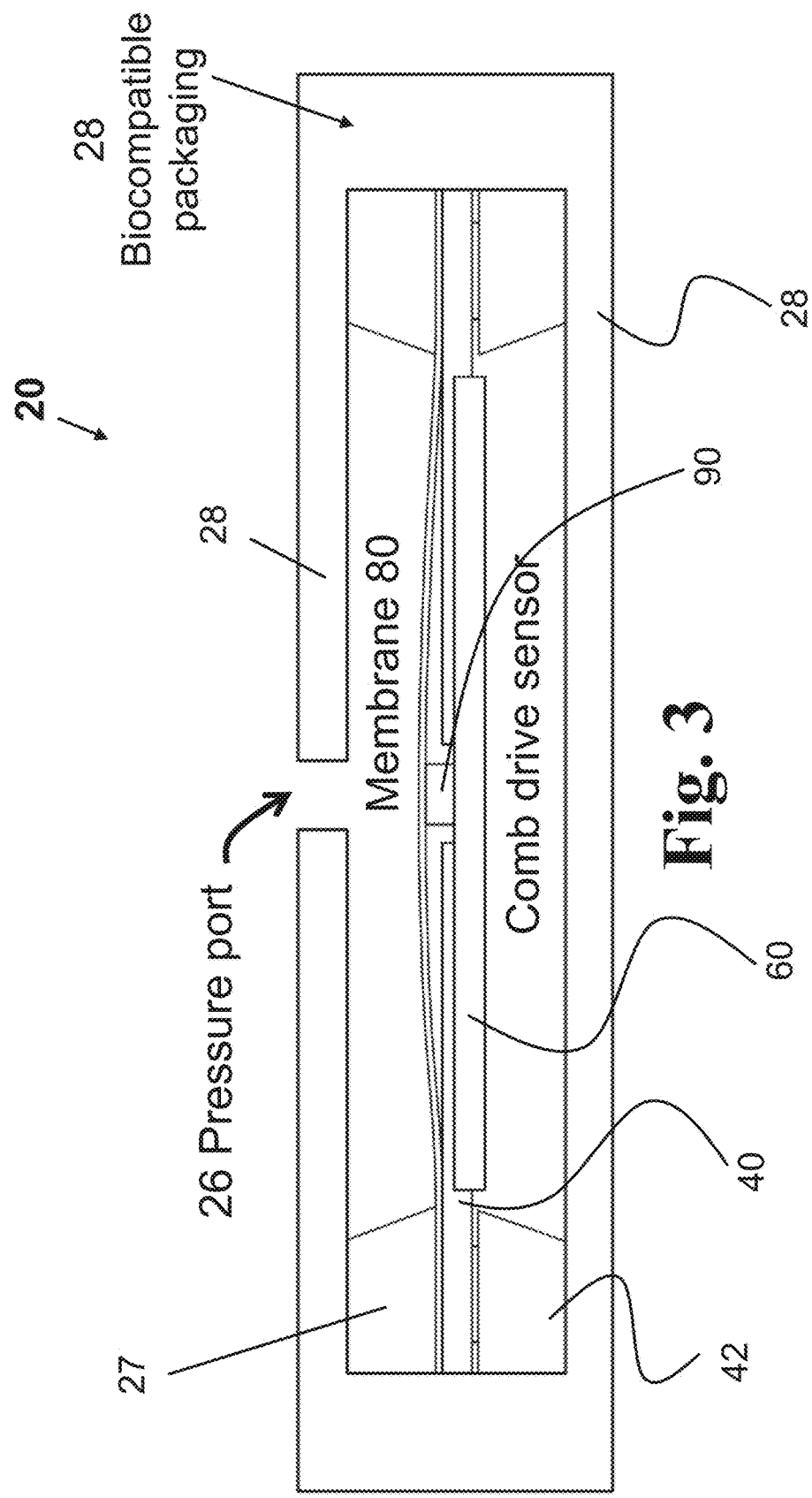
FIG. 3 is a cross sectional representation of a pressure sensor according to one embodiment of the present invention.

FIG. 3 is a schematic cross sectional representation of a sensor 20 according to one embodiment of the present invention. Sensor 20 includes a comb drive sensor comprising a rotor movable relative to a stator. The comb drive assembly is mounted within a housing, such that the stator is maintained at a fixed position within the housing, and the rotor is able to move relative to the stator.

FIG. 3 shows that sensor 20 includes two internal chambers separated by a flexible membrane or diaphragm. The top chamber is open to ambient conditions via a pressure port 26 located in a wall of the sensor enclosure 28. The other chamber of the sensor is a closed volume on the other side of diaphragm 80, this second volume including the comb drive sensor. Preferably, the second chamber is preloaded with a predetermined quantity of a gas, although yet other embodiments contemplate the application of a vacuum underneath membrane 80. FIG. 3 shows diaphragm 80 in a typical configuration in which it is prestressed and applying a substantial normal load by way of member 90 onto rotor 60. This initial condition of membrane 80 creates an initial offset in the rotor 60 relative to stator 40, which alters the working range of sensor 20, and can produce a substantially linear useful range of operation.

Figure 11A:
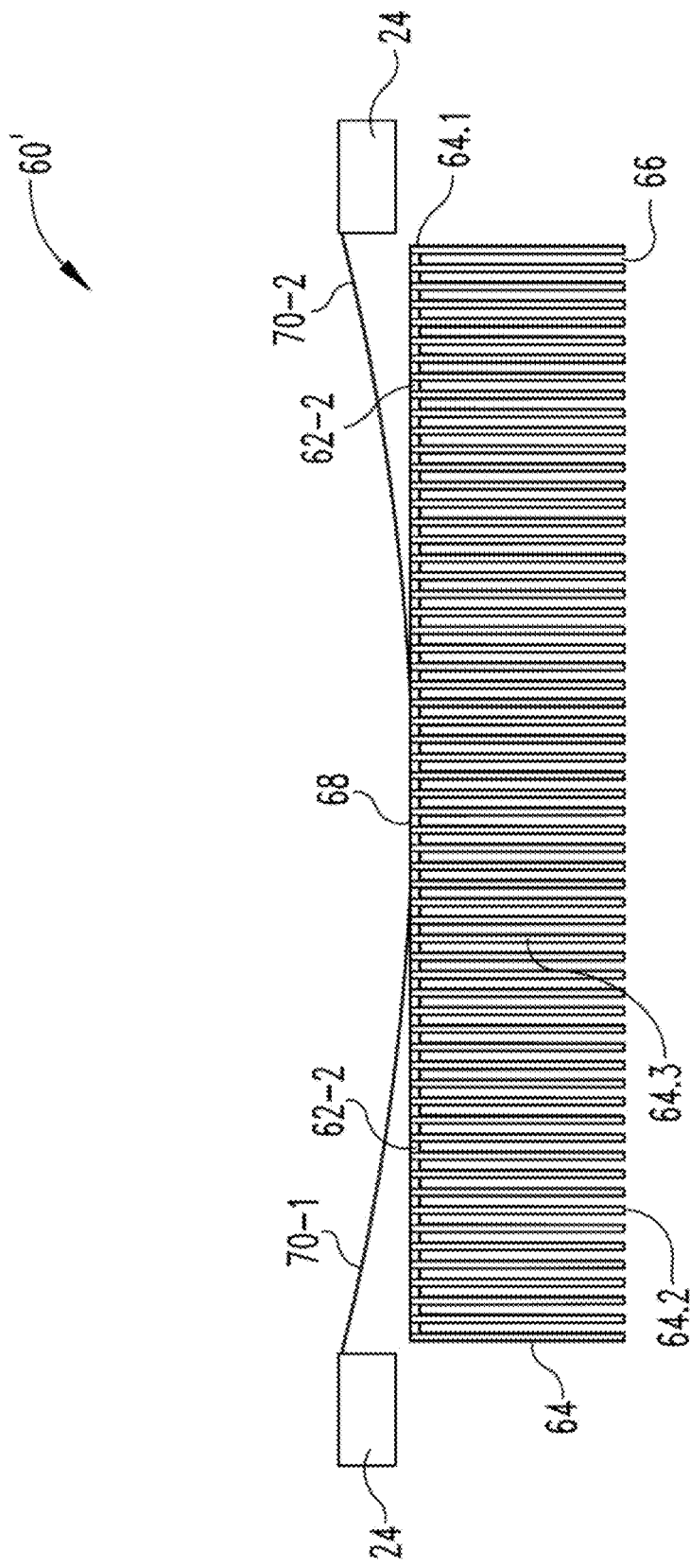
FIG. 11A is a side elevational view of the rotor of FIG. 10 shown in a deflected state.

FIGS. 4 and 5 show the rotor and stator, respectively, from the comb drive of FIG. 3. Referring to FIG. 4, rotor 60 includes a plurality of substantially planar blades 64 that extend laterally outward and preferably downward from a support arm 62. As was seen in FIG. 3, blades 64 extend downward from a support arm 62. FIG. 4 shows the top surface 64.1 of each blade 64. The inner edge 64.4 of each blade is preferably integral with a corresponding support arm 62. Each blade 64 extends laterally from the inner edge 64.4 to an outer edge 64.5. Referring briefly to FIG. 11A, it can be seen that each blade 64 extends vertically downward from a top surface 64.1 to a bottom edge 64.2, with a midsection 64.3 therebetween.

Rotor 60 includes right and left support arm 62-1 and 62-2 that substantially spam the length L of rotor 60. Each support arm 62 is adapted and configured to rigidly support a plurality of blades 64. In some embodiments, a first plurality of blades 64.1 extend laterally outward from a support arm 62-1, and a second set of blades 64.2 extend laterally in the opposite direction from a support arm 62-2. However, other embodiments of the present invention contemplate a single plurality of blades 64 that extend laterally across the entire width of rotor 60.

Each support arm 62 is adapted and configured to maintain each individual plate 64 in a substantially rigid orientation relative to adjacent plates. Each arm 62 is sufficiently stiff so as to maintain each blade 64 in parallel alignment, without substantial twisting or bending.

Each arm 62 is coupled to, and extends from, a central hub 68. Preferably, hub 68 and arms 62 are integral. Preferably, the coupling of arms 62 to hub 68 is sufficiently rigid such that each plurality of blades 64.1 and 64.2 (i.e., in and out of the plane of FIG. 4) without substantial twisting or bending. Referring to FIG. 4, in some embodiments each arm 62 can be considered as being cantilevered laterally outward from hub 68.

Hub 68 is preferably centrally located within rotor 60. Hub 68 is located about midway along the length L of rotor 60. Referring to FIG. 5, hub 68 is further located about midway across width W of stator 40.

Preferably, rotor 60 is adapted and configured to be mass balanced in two dimensions relative to hub 68. Referring to FIG. 4, it can be seen that a vertical line of symmetry taken through rotor 60 passes down the middle of springs 70-1 and 70-2. The mass of the rotor 60 to the left of this vertical centerline is preferably substantially the same as the mass of the rotor to the right of this centerline. Further, it can be seen that a horizontal centerline taken through rotor 60 would pass through the center of hub 68. The mass of rotor 60 above the horizontal centerline is preferably the same as the mass of rotor 60 below the centerline. By having the mass balanced about two orthogonal axes at the hub, the dynamic response of rotor 60 is enhanced. Any imbalance of rotor 60 about hub 68 can lead to increased flexing and twisting motion of plates 64, especially if the motion of rotor 60 approaches a resonant frequency. However, the present invention also contemplates those embodiments in which the mass of rotor 60 can be imbalanced in one or two dimensions about hub 68, especially in those applications in which dynamic response is not a concern.

Rotor 60 is supported relative to stator 40 by a pair of springs 70-1 and 70-2. Springs 70 are cantilevered inward from electrical contact pads 24. Pads 24 are preferably rigidly attached to and electrically isolated from rotor 60. In a structural sense, the springs 70 are coupled to "ground" at attachment pads 24. In some embodiments, the attachment of spring 70 to pad 24 can be viewed as a clamped connection, such that the boundary condition existing between a spring 70 and a connection pad 24 includes a predetermined angular relationship. In the sensors shown herein, this predetermined angular relationship is substantially perpendicular, although other embodiments of the present invention contemplate springs 70 that are attached to "ground" at any angle. However, in yet other embodiments, spring 70 may be coupled to pad 24 and stator 40 in a manner that can be viewed as a pinned arrangement, such that the boundary condition between the spring and "ground" is one of known displacement, but variable angle.

The other end of each spring 70-1 and 70-2 is cantileveredly attached to hub 68. Preferably, springs 70-2 and 70-2 are integrally formed with hub 68 during the MEMS fabrication process. Each spring 70 is preferably flexible as best seen in FIG. 11A. When a normal load is applied to pad 68, the arms 62 and blades 64 translate substantially as an integral unit. The translational movement of the arms and rotor is accompanied with flexing of each spring 70 relative to attachment pad 24, and further relative to hub 68. Each spring 70 preferably operates as a cantilever spring with the ends of each spring preferably integral with either a connection pad 24 or hub 68. In those embodiments in which spring 70-1 and 70-2 are substantially symmetric, the vertical movement of blades 64 (i.e., in and out of the plane of FIG. 4) is substantially translational. In some embodiments, the arrangement of the suspension system (springs 70 and their manner of attachment) substantially guides the vertical movement of rotor 60, with only insubstantial lateral movement or twisting.

In some embodiments, the cross sectional shape of each spring 70 is substantially that of a rectangle. In those applications in which the width of the base b of the rectangle is greater than the height h, the spring 70 will have a first vertical spring constant that is softer than the lateral spring constant. Referring to FIG. 4, a spring 70 having a rectangular cross section where the height of the spring (same as the depth of the spring as viewed in FIG. 4) is less than the width of the spring, then lateral motion (i.e., left to right in FIG. 4) is minimized because of the higher spring constant in that direction. Further, motion of the rotor 60 from top to bottom of FIG. 4 is minimized by the state of tension created on spring 70. Therefore, the direction of greatest flexibility of rotor 60 is in and out of the plane of FIG. 4.

FIG. 5 is a top planar view of a stator 40 that combines with rotor 60 to create a comb drive. Stator 40 includes a first conductive pad 22 that is in electrical communication with a plurality of plates 44 extending laterally inward toward the center of stator 40. Each plate 44 is spaced apart by its adjacent plates by a channel 46. Channel 46 is adapted and configured to receive within it a single blade 64. Likewise, each plate 44 is received within the gap 66 between adjacent blades.

Stator 40 further includes a support structure 42-1 on one side of the open midsection, and a section support 42-2 that supports plates on the other side of the open midsection. The midsection of stator 40 is open so as to permit the free movement of springs 70, arms 62, and hub 68. Each plate 44 includes a top edge 44.1, a bottom edge 44.2, and a midsection 44.3 therebetween (the latter being best seen in FIG. 6B).

FIGS. 6A and 6B show portions of a sensor 20 both uncoupled, and assembled, respectively. FIG. 6a shows a comb drive including a stator 40 and rotor 60 generally supported by rotor support 42. The first electrically conductive common 22 is insulated from the second electrically conductive common by an insulator, such as a two micron layer of silicon dioxide.

FIG. 6A further shows that sensor 20 includes in some embodiments a diaphragm or membrane 80 that is coupled to supports 27 that are rigidly held within enclosure 28. In some embodiments, diaphragm 80 is fabricated from silicon dioxide, although any MEMS-suitable and biocompatible material can be used. In some embodiments, diaphragm is preferably in a substantially flat, planar, free state attached to supports 27. However, the invention is not so constrained, and also contemplates diaphragms or membranes 80 that have a non-flat shape in the free (unstressed) state.

Sensor 20 preferably includes means for coupling the diaphragm 80 to the rotor 60. In some embodiments, this coupling is accomplished by a link, or member, or coupler 90 that is placed inbetween the underside of diaphragm 80 and the top side of hub 68. In some embodiments, coupling 90 is integral with diaphragm 80. In yet other embodiments, the member 90 is integral with hub 68. Preferably, the means for coupling is attached to only one of the diaphragm or hub, and is not attached to the other. Further, the shape and size of link 90 is adapted and configured so as to impose only a normal force (i.e., perpendicular) between diaphragm 80 and rotor 60. In such embodiments, the coupler 90 is adapted and configured so as to apply only a normal load or a load in one direction, and unable to substantially apply any other type of load. For example, in some embodiments, coupler 90 cannot impart lateral sliding motion to rotor 60. Further, in some embodiments, coupler 90 is unable to impose any twisting or flexing motion of diaphragm 80 into rotor 60. In these embodiments, even if there are non-uniformities or imperfections in the arrangement of the diaphragm coupler relative to the rotor, only a substantially normal load can be imposed from diaphragm 80 onto rotor 60.

In some embodiments, rotor 60 is located relative to coupler 90 and diaphragm 80 such that the assembly of the diaphragm to the comb drive results in an initial, prestressed state of diaphragm 80. In this manner, and as best seen in FIG. 6B, the flexure of diaphragm 80' acts on member 90 so as to initially offset each blade 64 within its corresponding channel. Each midsection 64.3 of the blades of rotor 60 is offset from the midsection 44.3 of the plates of stator 40. In this manner, the comb drive has an initial overlap of the blades relative to the plates that is less than the full overlap. As is known to one of ordinary skill in the art, it is the overlapping of the electrically conductive blades of rotor 60 with the electrically conductive plates of stator 40 to store electrical charge in any dielectric located therebetween.

However, yet other embodiments of the present invention also contemplate embodiments in which the initial offset of the rotor relative to the stator is accomplished by angular offsets in the connection of the springs 70 to either or both of the connection pads 24 or hub 68.

Figure 7:
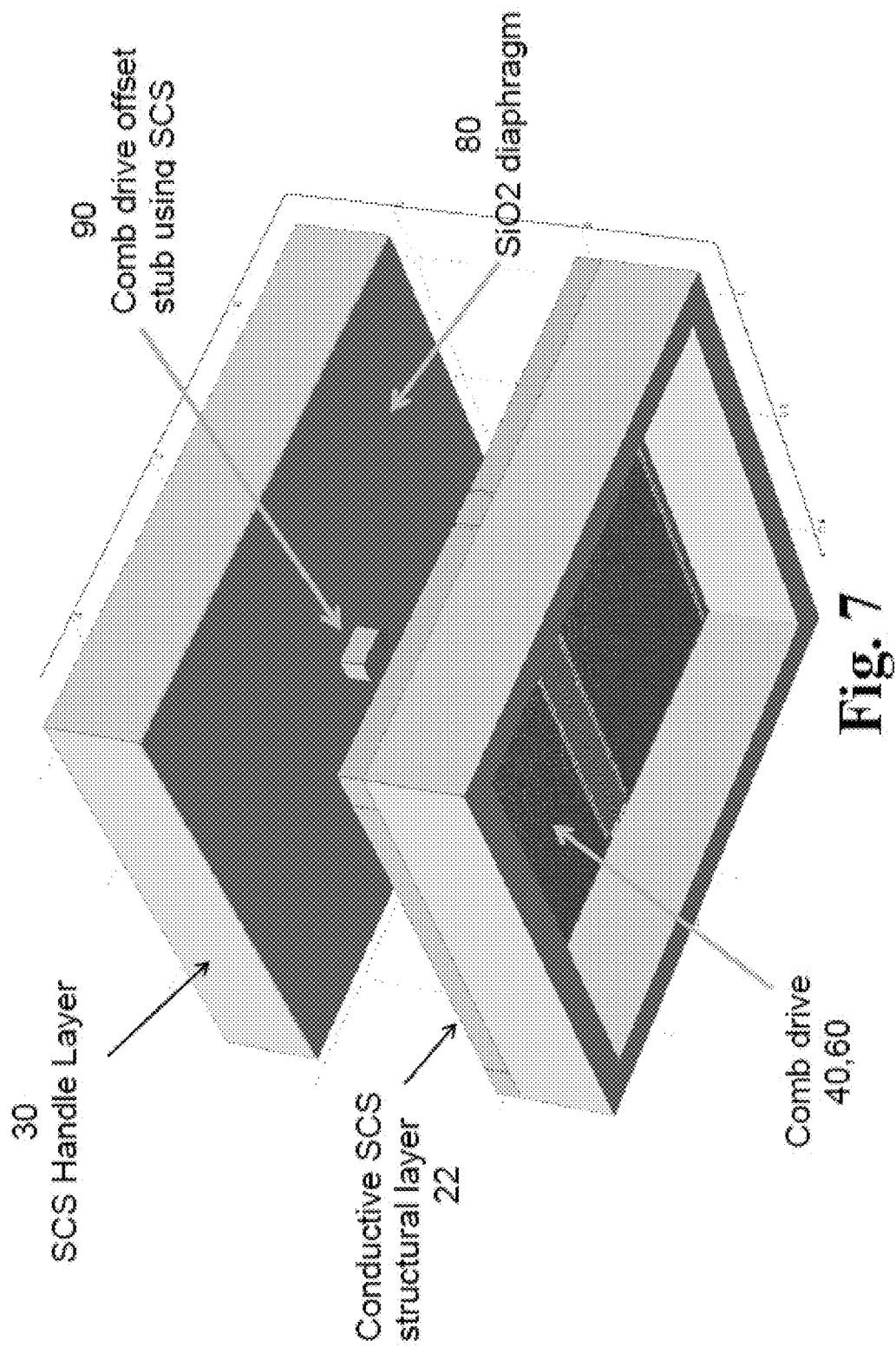
FIG. 7 is an exploded, perspective schematic representation of the transducer of FIG. 3 at a first viewing angle.
Figure 8:
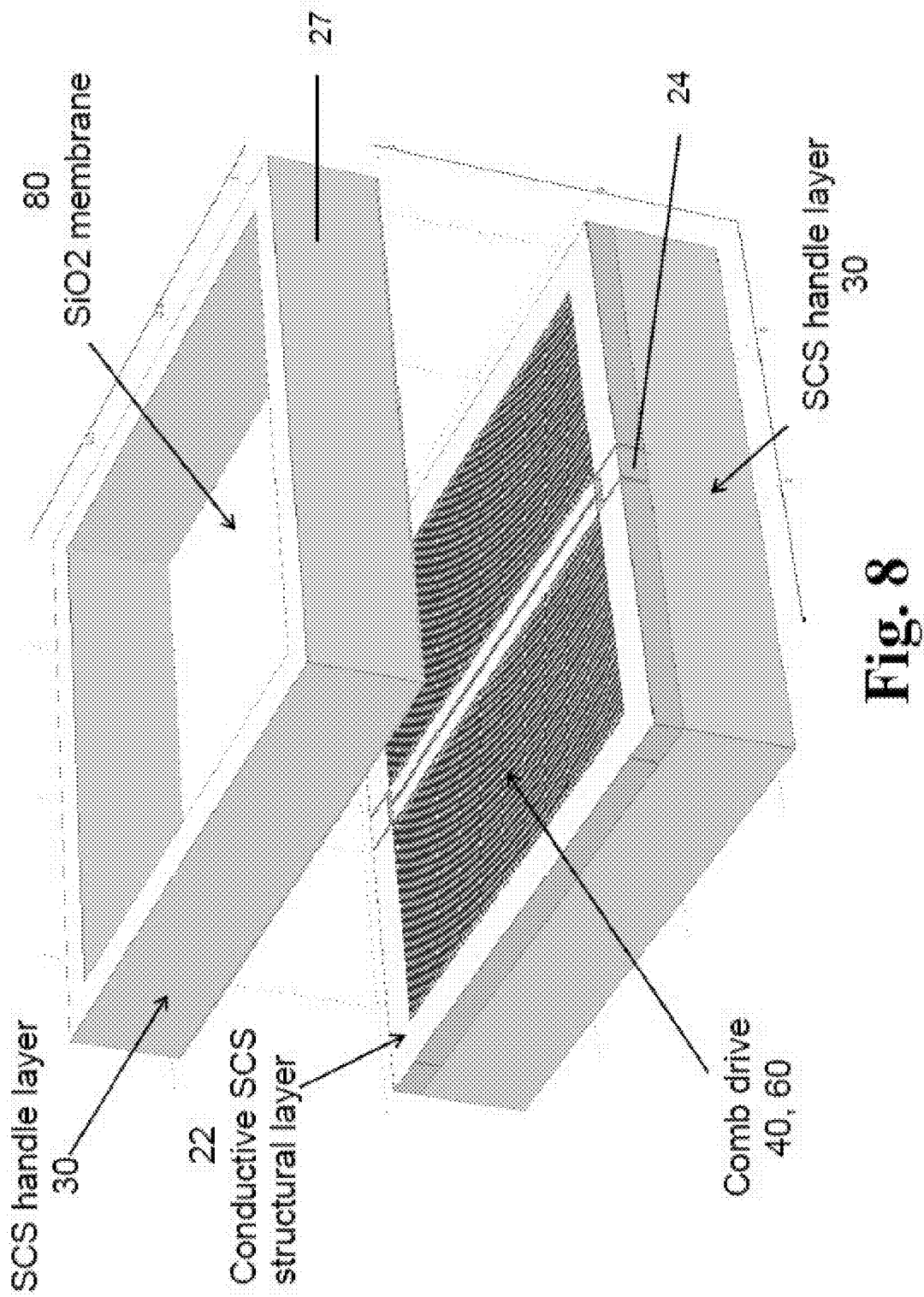
FIG. 8 is an exploded, perspective schematic representation of the transducer of FIG. 3 at a second viewing angle.
Figure 9:
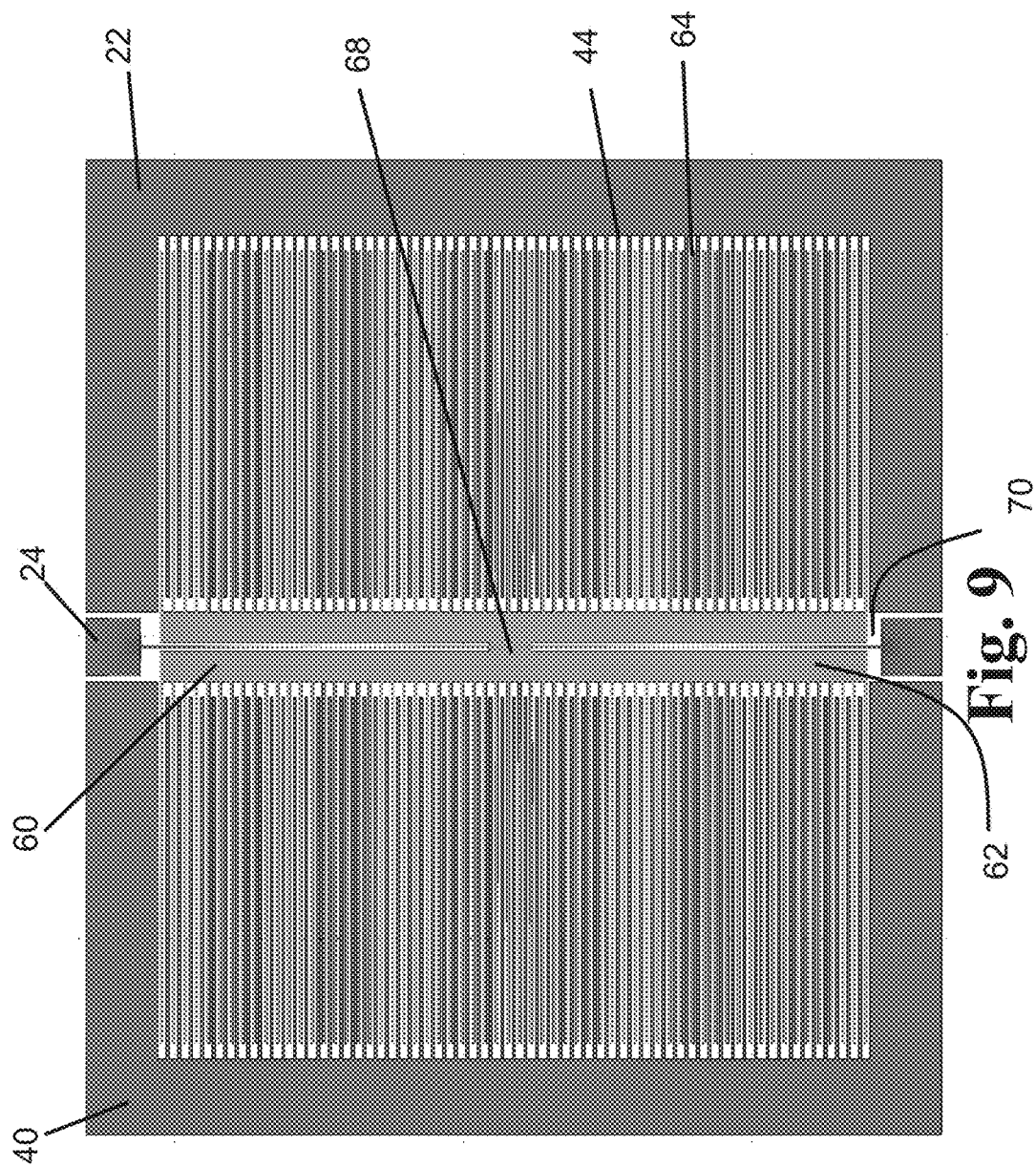
FIG. 9 is a top plan view of the assembly of the rotor and the transducer of FIG. 3.
Figure 10:
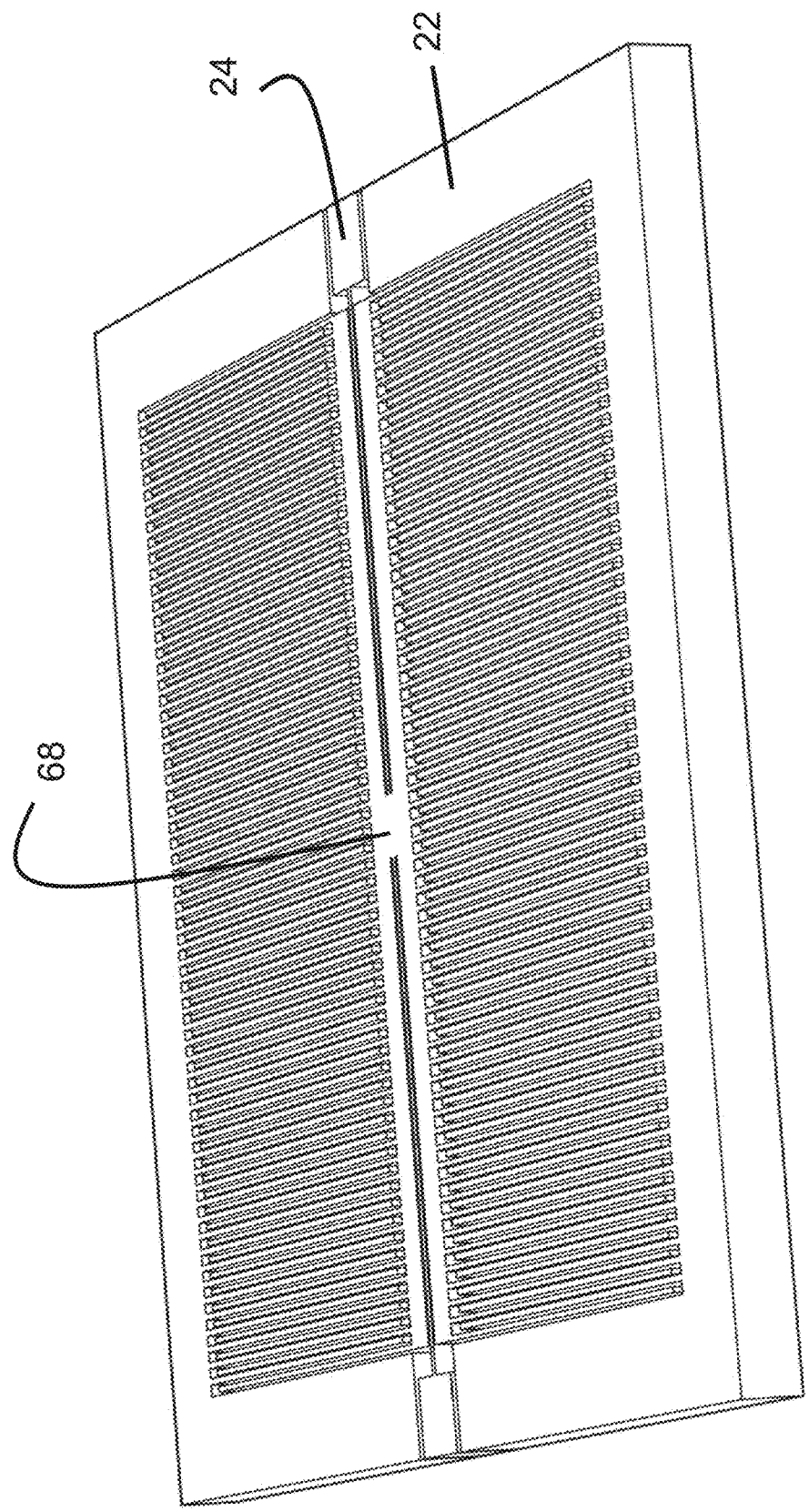
FIG. 10 is a side perspective view of the assembly of FIG. 9.

FIGS. 7 and 8 show perspective, three dimensional depictions of the components of FIG. 6a. It can be seen that membrane 80 has substantially the same plan form as the comb drive shown in FIGS. 4 and 5. Further, FIG. 9 is a plan form looking downward on the comb drive. FIG. 10 presents a perspective view of the comb drive of FIG. 9.

Figure 11B:
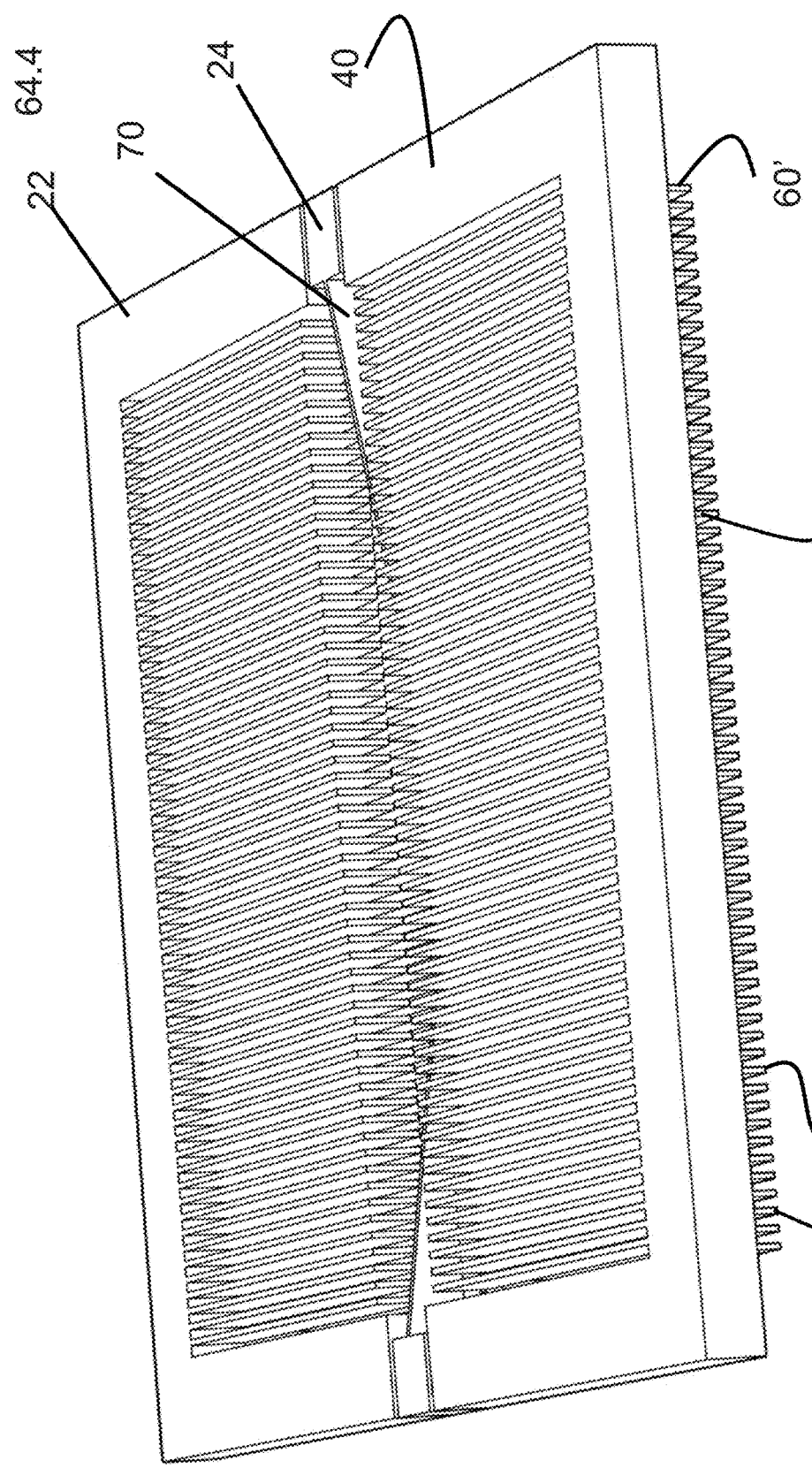
FIG. 11B is a view of the apparatus of FIG. 10 with the rotor in a deflected state.

FIGS. 11A and 11B show cross sectional and perspective views, respectively, of the comb drive. FIG. 11A shows that the imposition of a normal load from a link 90 onto base 68 results in generally downward translation of plates 64 and support arms 62. As best seen in FIG. 11B, it can be seen that the outer edges 64.5 of the plates generally translate without twisting or flexing relative to the inner edges 64.4.

Pressure sensors according to some embodiments are fabricated using the standard SOI Multi User MEMS Process, fabricated by MEMSCAP™. Devices according to some embodiments of the present invention include subassemblies: an upper diaphragm (80) and a lower comb drive sensor (40, 60). These two subassemblies are depicted in FIGS. 6A and 6B, where FIG. 6A depicts the separated pair, and FIG. 6B depicts the resulting cross section after the pair is bonded together. It can be seen that a 20 micron post, length, or coupler 90 produces an initial offset for the comb drive. FIGS. 7 and 8 show 3D views of the separated pair. Both the comb drive (40, 60) and the 20 micron post are features of some embodiments of the present invention.

A simulation showing the comb drive portion of the pressure sensor is shown in FIGS. 9, 10 and 11. FIG. 9 shows a top view of the comb drive in which rotor 60 deflects out-of-plane. The fixed-fixed flexures 70 can also be seen along the center backbone arm 62 of the comb drive array. The fixed-fixed flexures 70 provide an increase in robustness for the wafer bonding process, and the flexures decrease the possibility of comb finger pull-in failure. FIGS. 10 and 11A and 11B show the states of the comb drive before and after a deflection.

Figure 12:
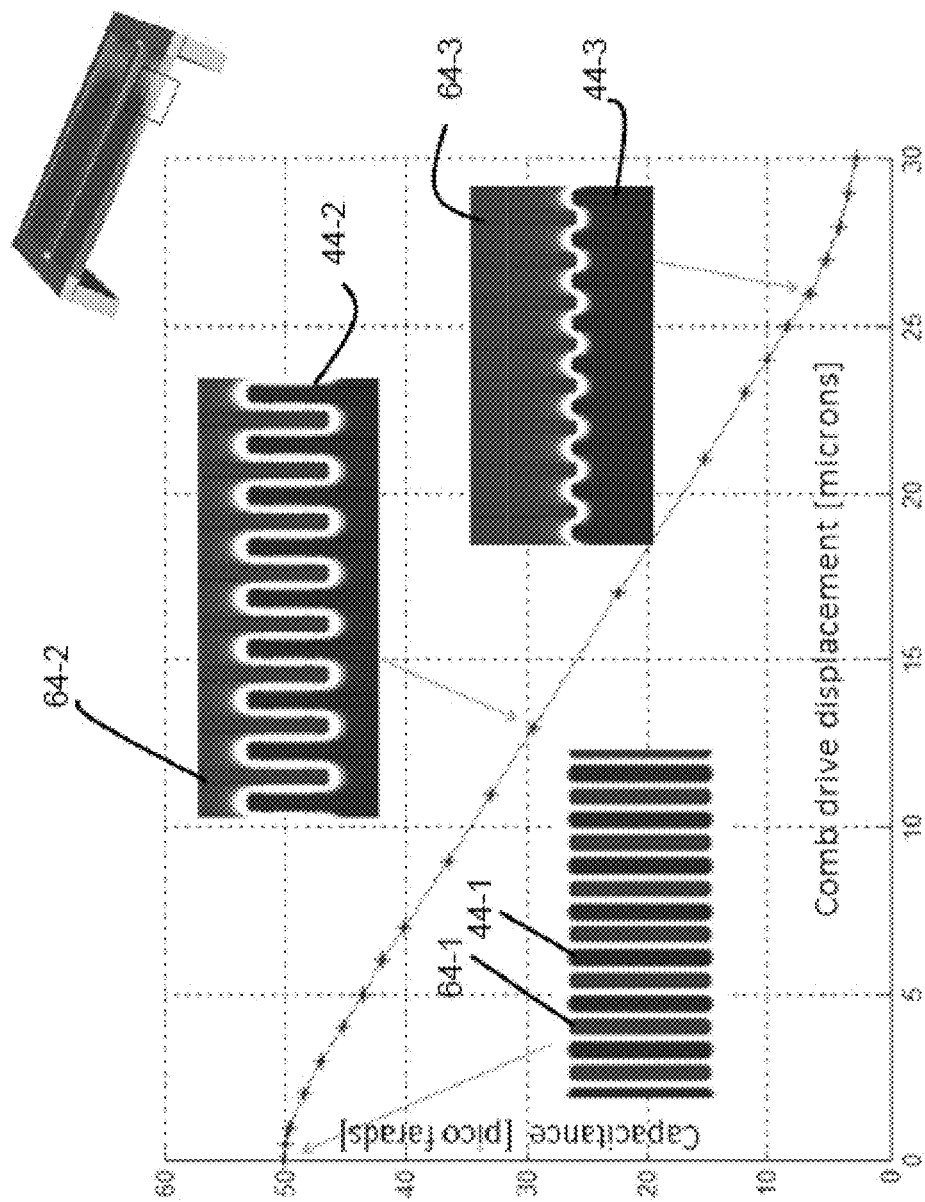
FIG. 12 is a graphical representation of the capacitance of a sensor according to one embodiment of the present invention as a function of rotor and stator relative displacement.

For pressure sensor use in infants, the elderly, or the strongest of adults, the sensor should be sensitive enough for low lung pressures as well as be robust enough to withstand maximal lung pressures, ranges of which are shown in FIGS. 12, 13, and 14. Investigating a cross section of the comb drive (see FIG. 12), there is a plot of capacitance as a function of displacement from full comb finger engagement to full comb finger separation. As seen in FIG. 12, the first 3 to 4 microns are nonlinear. It is for this reason that the post 90 establishes an initial offset for a full linear operating range. Capacitance versus lung pressure and diaphragm deflection versus lung pressure are shown in FIGS. 13 and 14. A maximal pressure of 50 mmHg is shown to be within the linear operating range of a pressure sensor. The capacitance to deflection sensitivity is found to be 0.5 picofarads per mmHg, in some embodiments of the present invention. Therefore, a capacitance meter (with a 4 attofarad capacitance resolution) can discern a pressure change as small as about 2e-6 mmHg.

Referring to FIG. 12, the capacitance for a sensor according to one embodiment of the present invention is shown toward the left of the chart, in which the blades 64-1 have substantial overlap with plates 44-1. In the middle of FIG. 12 the blades 64-2 are shown to have less overlap with plates 44-2, such that the capacitance of the sensor has diminished to about midrange. The graphical depiction toward the right of FIG. 12 shows that the blades 64-3 have little overlap with plates 44-3, such that little charge is retained in the capacitive sensor. As the blades move toward even lower levels of overlap (such as for displacements in excess of 27 microns) that the amount of planar area in effect is substantially reduced and edge effects become more significant.

Figure 13A:
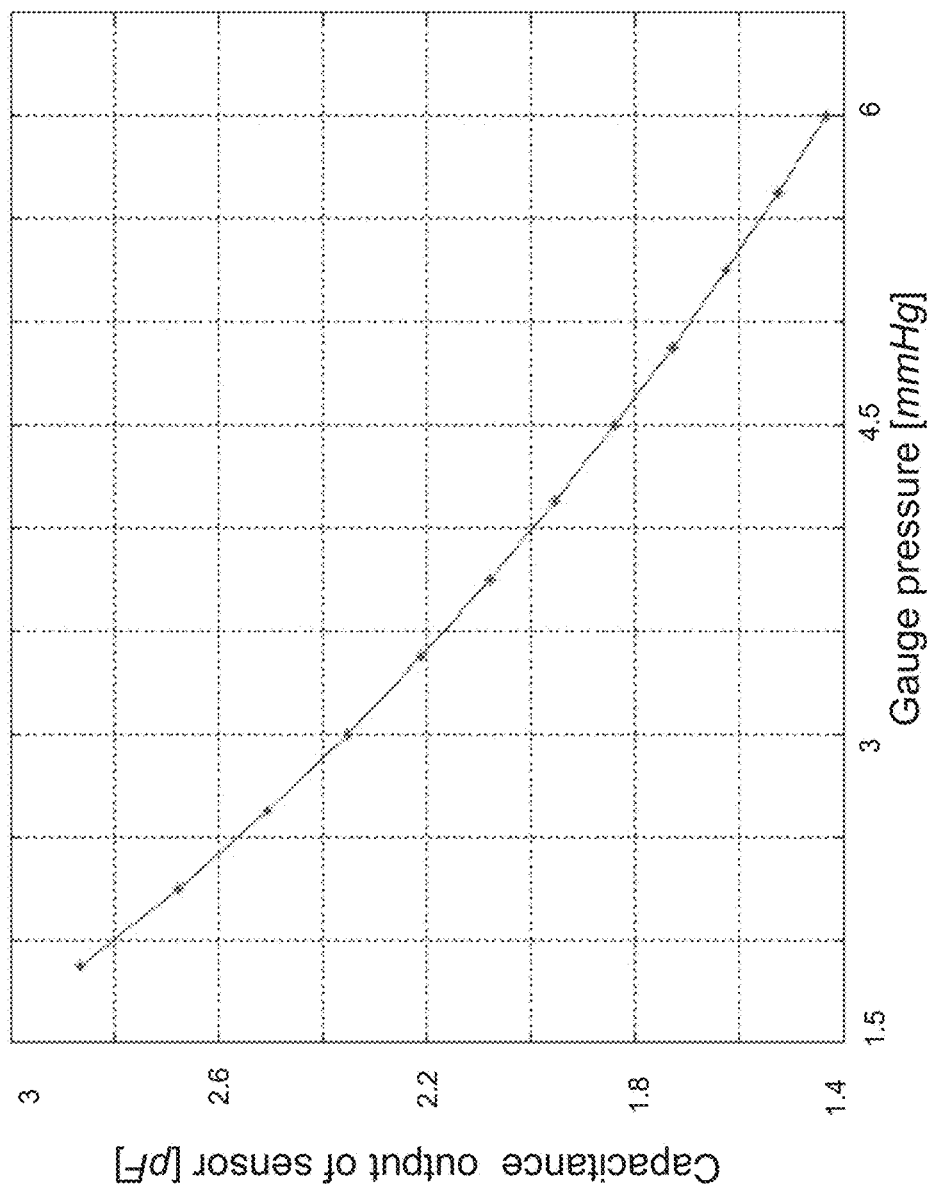
FIG. 13A is a graphical representation of sensor capacitance as a function of gauge pressure according to one embodiment of the present invention.
Figure 13B:
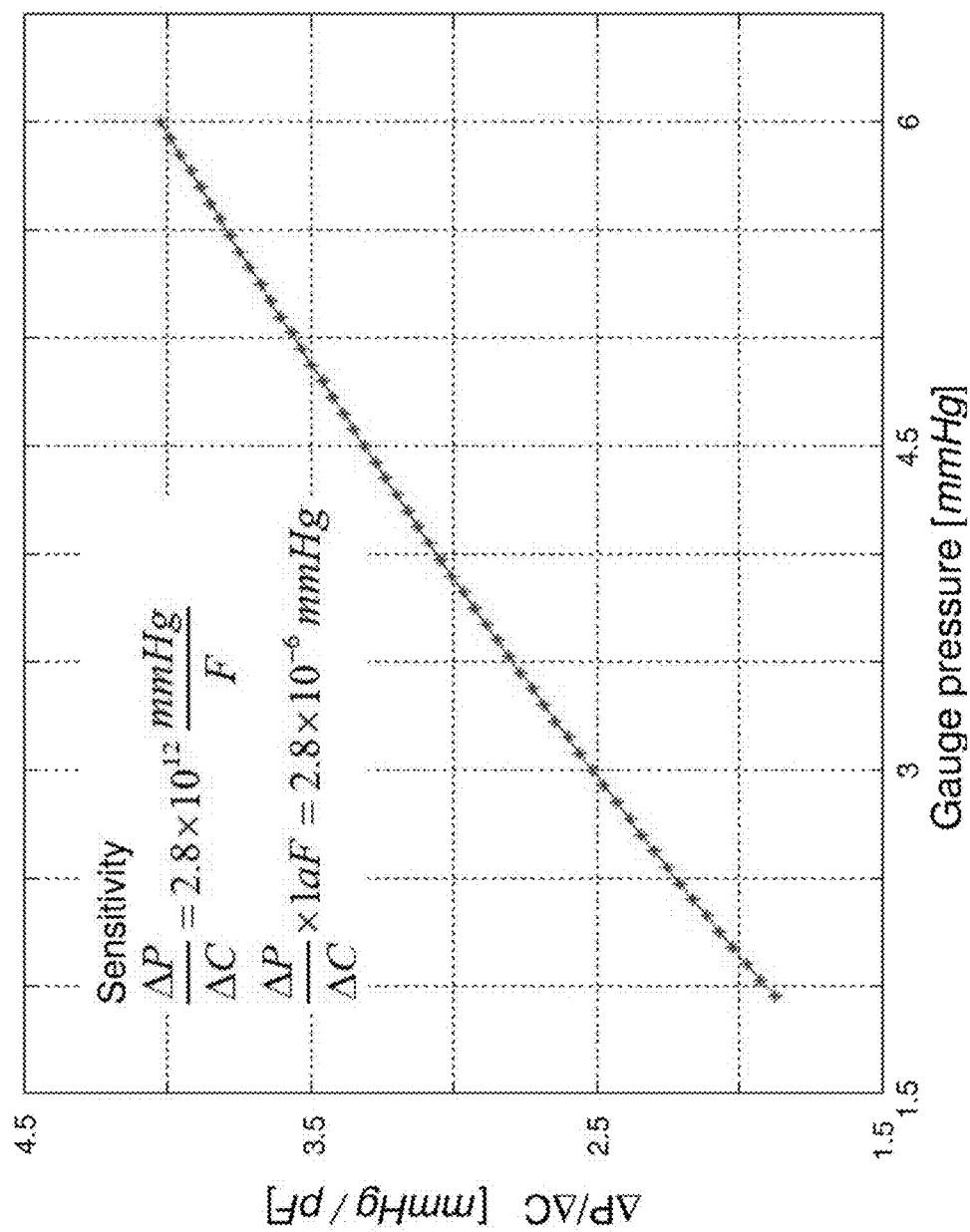
FIG. 13B is a graphical representation of the sensitivity of the sensor according to one embodiment of the present invention.

FIGS. 13A and 13B are graphical representations of the variable capacitance of a sensor according to one embodiment of the present invention. FIG. 13A shows the capacitance of the sensor (the amount of charge retained between midsections of adjacent blades and plates) as a function of gauge pressure. It can be seen that in a pressure range of interest, the capacitance of the sensor has about a 2 to 1 change. FIG. 13B calculates the sensitivity of the output shown in FIG. 13A. It can be seen that the sensor changes sensitivity by a ratio of about 2 to 1 over a pressure range of interest.

Figure 14A:
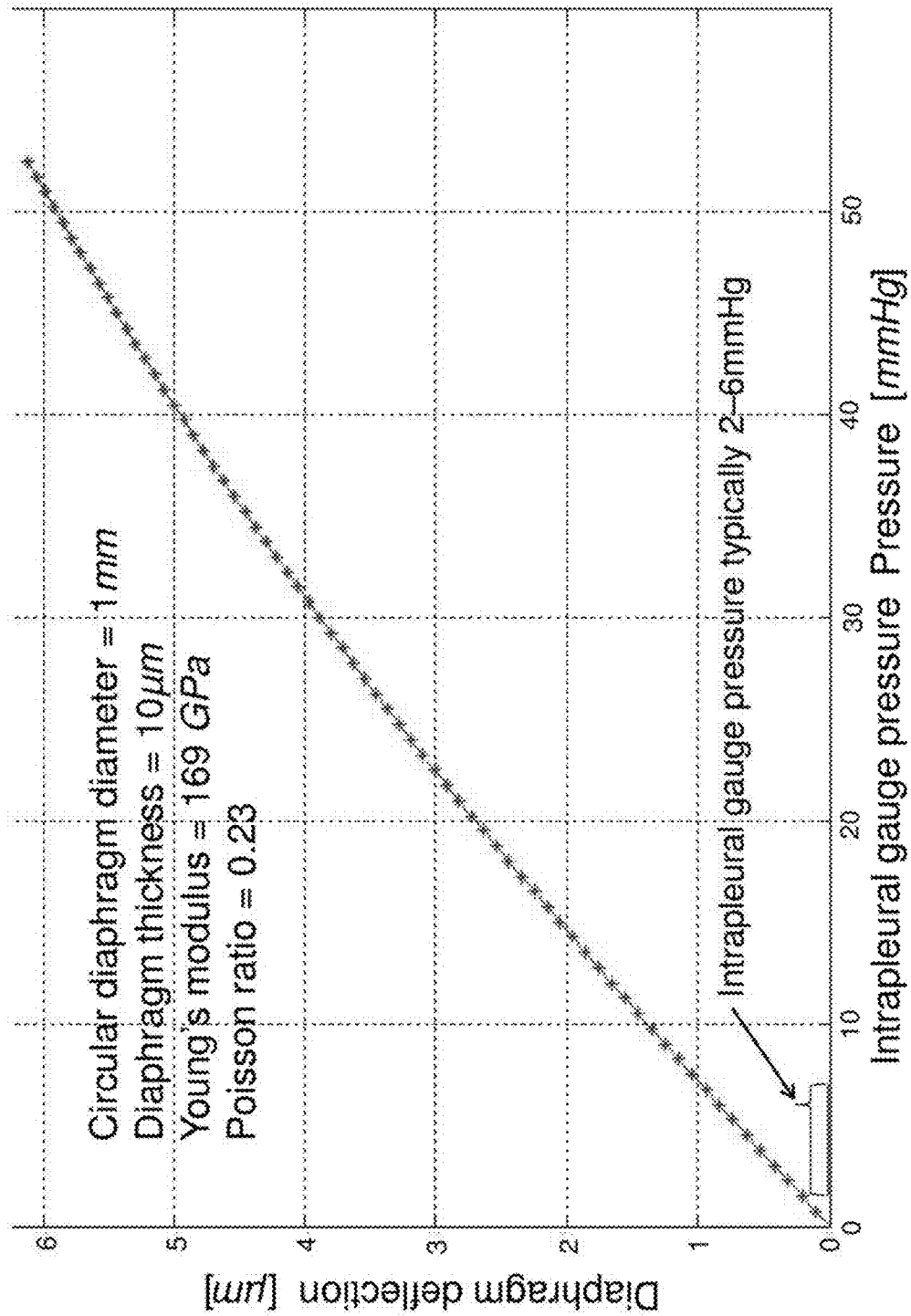
FIG. 14A is a graphical representation of diaphragm deflection as a function of intrapleural gauge pressure for a sensor according to one embodiment of the present invention.
Figure 14B:
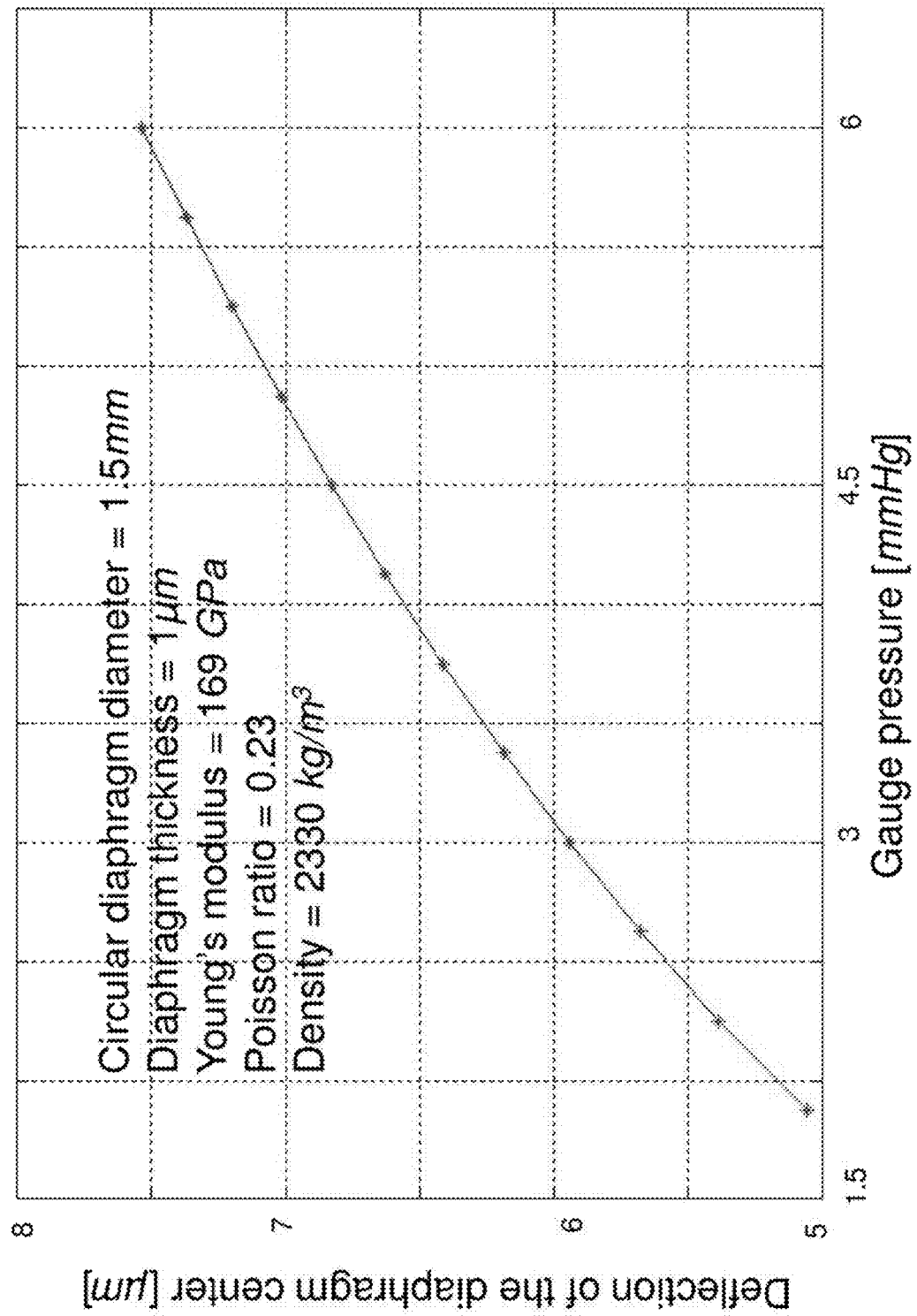
FIG. 14B is a graphical representation of diaphragm deflection as a function of intrapleural gauge pressure for a sensor according to one embodiment of the present invention.

FIGS. 14A and 14B pertain to deflection calculation made for a circular diaphragm 180 for sensor 120. FIG. 14A pertains to a diaphragm of 1 mm in diameter and about 10 microns thick. FIG. 14B refers to a diaphragm of 1½ mm, with a thickness of 1 micron. It can be seen that a diaphragm according to some embodiments of the present invention can be tailored to various ranges of gauge pressure.

FIGS. 15-20 depict portions of a sensor 120 according to another embodiment of the present invention. FIG. 15 shows a generally circular rotor 160. Four pads 124 are arranged equally around, and on opposite sides of, a central base 168. Base 168 is supported by springs 170-1, 170-2, 170-3, and 170-4. As was the case with sensor 20, the suspension system of rotor 160 establishes uniform vertical motion for a load imposed upon hub 168.

The blades 164 of rotor 160 is arranged in substantially equal quadrants. It can be seen that the outermost blades 164 are radially outward the greatest distance from hub 168, and therefore have the greatest circumference. The innermost blades 164 are short in comparison, but preferably all blades within a quadrant extend over a 90 degree circular arc.

Although what is shown and described is a rotor 160 arranged in four equal circular quadrants, it is understood that other embodiments of the present invention are not so limited. Other embodiments of the present invention contemplate fewer "pie-shaped" sectors, or more sectors. Preferably, the rotor retains mass balance in two dimensions, such that the weight and mass distribution of the blades of each sector are substantially the same.

The configuration of rotor 160 has increased stability and stiffness relative to any lateral movement of the rotor. For example, any tendency to pull rotor 160 toward the left in FIG. 15 would be resisted by tension within arm 170-1. Therefore, in some embodiments, springs 170 have substantially uniform cross sections (such as square or round). The additional lateral stability of a rectangular cross section is not needed in some of these embodiments. Further, although a circular shape has been shown and described, other embodiments of the present invention contemplate yet other plan forms, including oval and triangular.

FIG. 16 is a top plan view of a stator 140 according to another embodiment of the present invention. Stator 140 includes four sectors of plates 144 arranged in quarter circles about a central axis. Plates 144 are substantially equidistance from one another, and therefore define a channel 146 that receives within it a corresponding blade 164. Each of the four sectors are united in common electrical communication via pads 122 and other conductive paths not shown.

Figure 17:
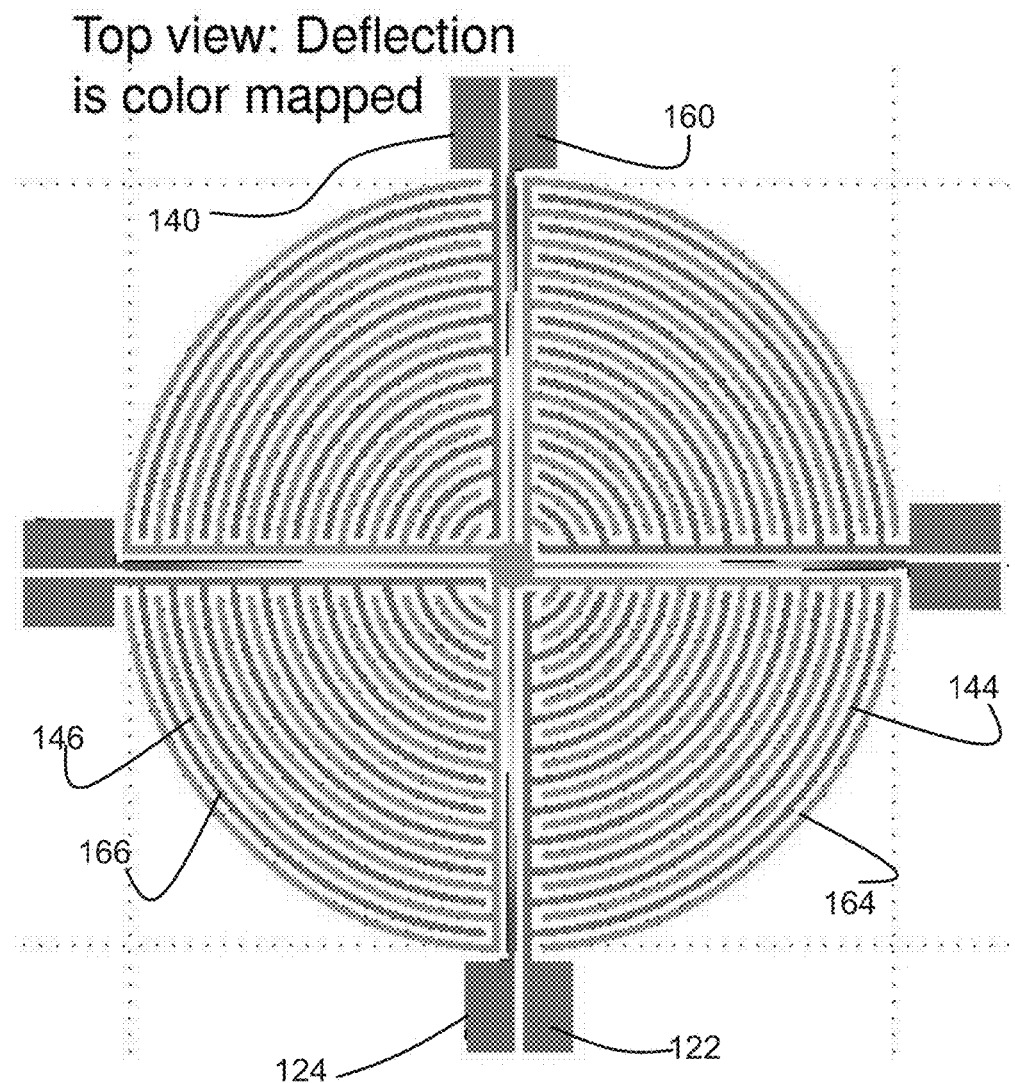
FIG. 17 is a top plan view of the subassembly of the rotor and stator of FIGS. 15 and 16, respectively.
Figure 18:
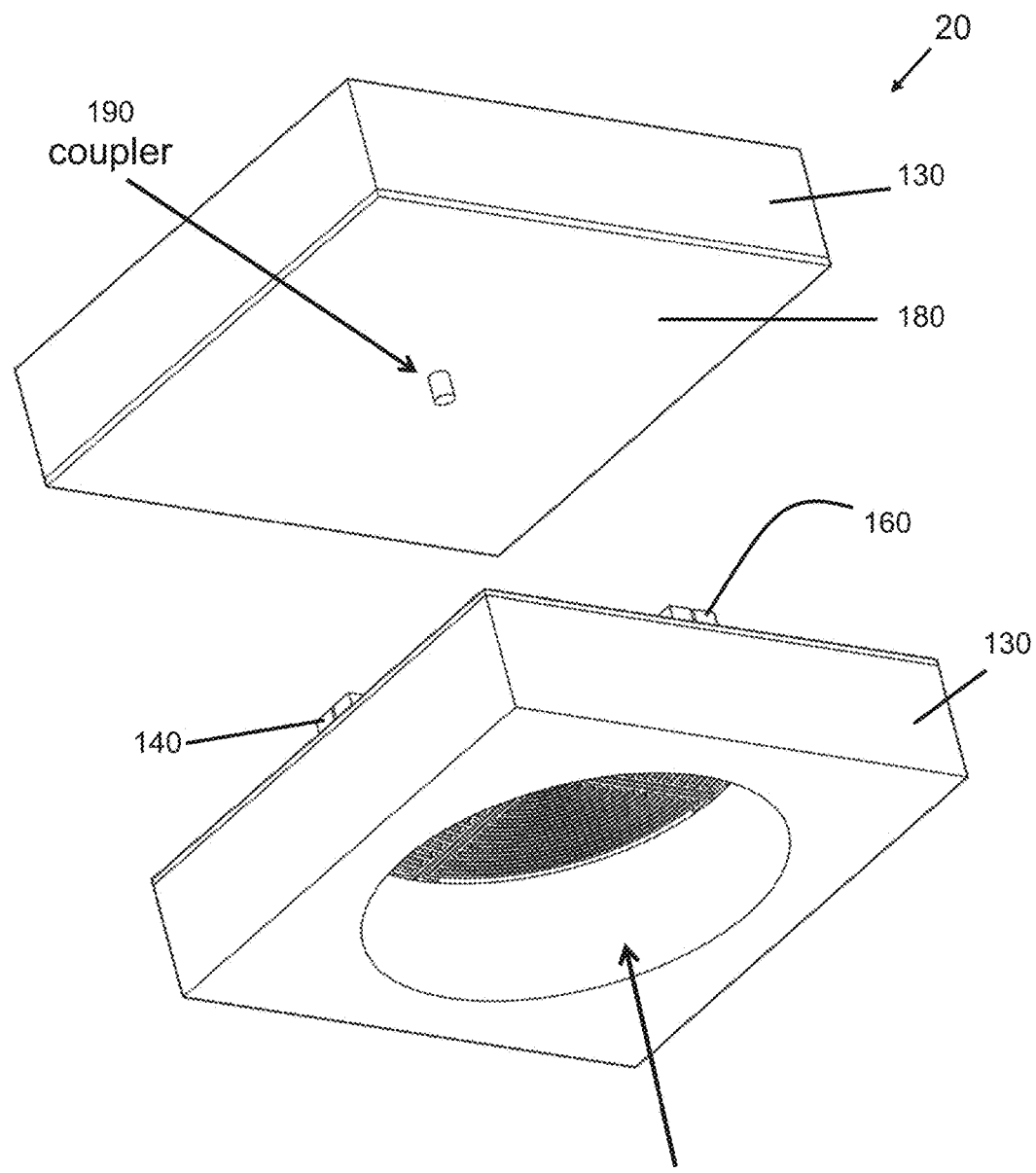
FIG. 18 is an exploded, perspective view of a sensor incorporating the rotor and stator assembly of FIG. 17 from a first viewing angle.

FIG. 17 is a top plan view of a rotor 140 combined with a stator 160 to produce a comb drive for a sensor 120. FIG. 18 is an exploded perspective view of a three dimensional representation of a sensor 120. A coupler, link, or member 190 is attached to, or integral with, a diaphragm 180 that is attached and sealed at its edges to an internal support 130. Although diaphragm 180 has been shown with a square plan form, it is understood that round plan forms and other shapes are also suitable.

Figure 19:
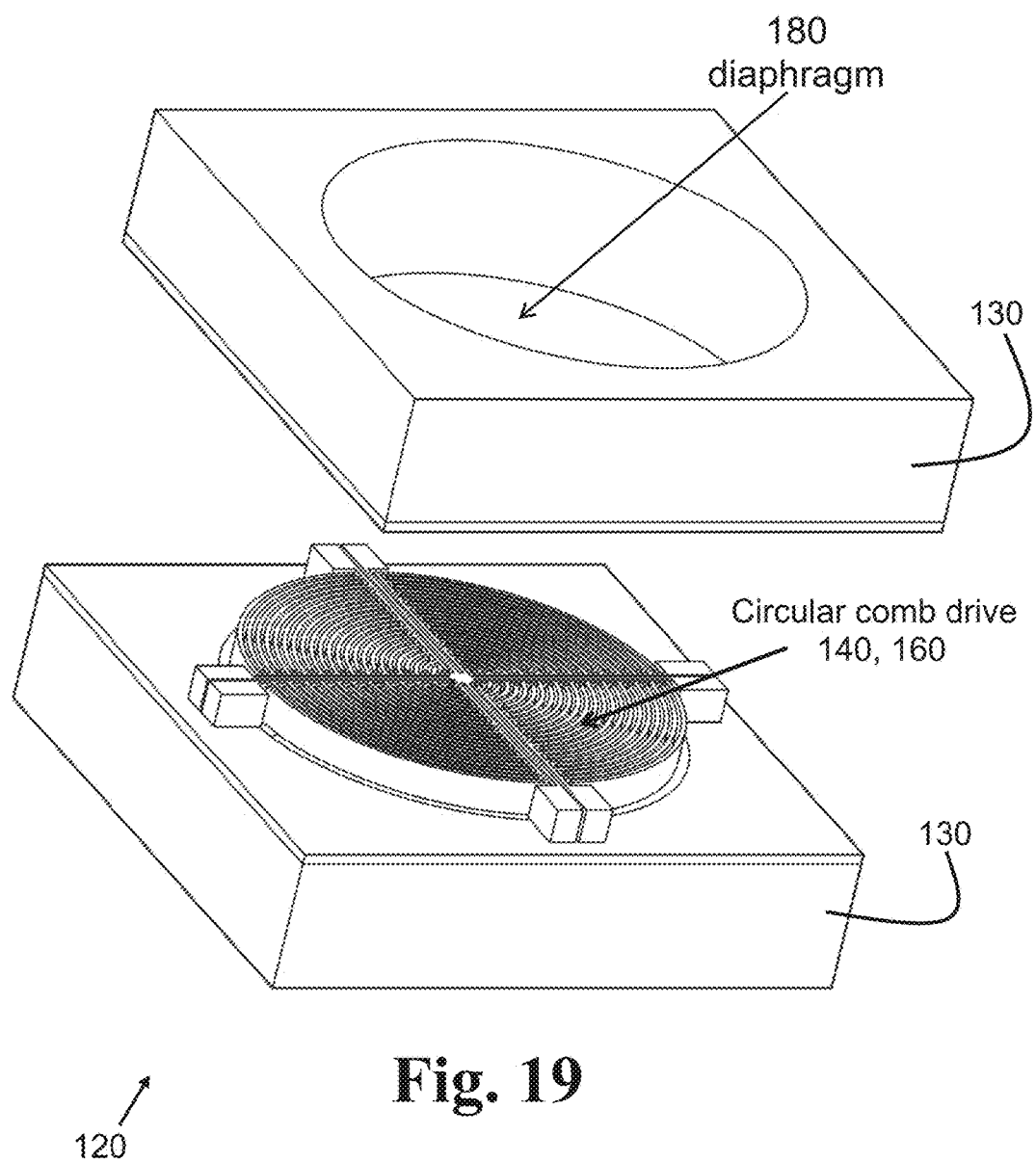
FIG. 19 is an exploded, perspective view of a sensor incorporating the rotor and stator assembly of FIG. 17 from a second viewing angle.

As best seen in FIG. 19, sensor 120 comprises the assembly of the supported diaphragm and the circular comb drive (in similar manner to that shown in FIG. 3). It is understood that the support 130 for diaphragm 180 is contoured to fit on top of the bottom support 130 that holds the comb drive, such that in the final assembly the diaphragm provides a hermetically sealed cover to the comb drive.

Figure 20:
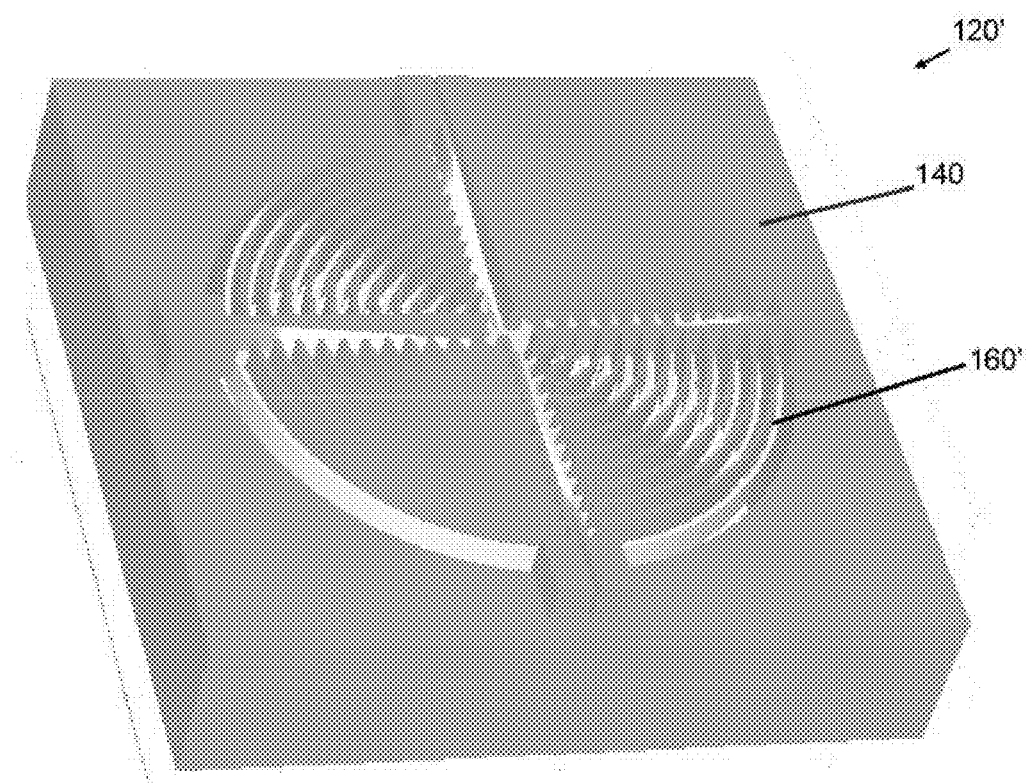
FIG. 20 is a top perspective view of a portion of an assembled transducer incorporating the rotor and stator assembly of FIG. 17.

FIG. 20 shows a sensor 120' in a deflected state. A normal load has been imposed on hub 168, and therefore rotor 160' deflects downward in a substantially vertical manner. The springs 170 connecting hub 168 to pads 124 can be seen flexing because of the imposed normal load.

Although what has been shown and described are sensors 20 and 120 of particular configurations, the present invention contemplates those embodiments in which a variable capacitor comprises a pair of comb drives stacked one on top of another. Further, the major internal components of the sensor can be stacked one on top of another. As one example, a sensor 220 includes a single diaphragm 280 suspended between a top comb drive (including a rotor 260-1 and a stator 240-1), and a bottom comb drive (comprising a rotor 260-2 and a stator 240-2). In one embodiment, the centrally located diaphragm 280 includes an upper coupling 290-1 that applies a load to base 268-1, and a bottom coupler 290-2 that applies the opposite load to base 268-2. When a pressure differential is applied to diaphragm 280, it flexes in one direction, which creates a compressive normal load onto one of the bases. If the opposite coupling member is adapted and configured to permit application of a tensile load, then in the other direction the diaphragm will pull upon the opposite rotor. Therefore, the top and bottom comb drives move oppositely relatively to their stator when the diaphragm deflects. Sensor 220 is a sensor in which the comb drives are inverted in their orientation.

In yet another embodiment, a sensor 320 includes a pair of stacked comb drives that retain the same relative orientation, and are simply stacked one on top of another. In such applications, the diaphragm 380 pushes downward on each rotor 360-1 and 360-2, by a member 390 that is in contact with both bases 368-1 and 368-2. The upper base 368-1 can include a centrally located aperture that permits a portion of the coupling member 390 to extend downward toward the lower base 368-2. Coupling member 390 preferably includes an upper portion of greater diameter that presses against upper base 336-1.

What follows are paragraphs S1, S2, and S3 that express particular embodiments of the present invention. In those paragraphs that follow, the element numbers are prefixed with an "X" indicating that the words in some cases pertain to any of the features shown in the drawings or described in the text.

S1. A microfabricated variable capacitor, comprising:

a stator (X40) including a plurality of electrically conductive plates each spaced apart from one another, each said pair of adjacent plates forming a channel therebetween, each of said plates being in a first common electrical communication;

a rotor (X60) including central hub (X68) and first and second arms (X62) extending in cantilever manner from said hub, a first plurality of electrically conductive blades being coupled to said first arm and a second plurality of electrically conductive blades being coupled to said second arm, each of said first plurality and said second plurality of blades being in a second common electrical communication; and wherein said hub is suspended from said stator by first and second springs (X70), such that each of said blades is received within a corresponding one of said channels and a portion of each said blade coacts with an adjacent said plate to store electrical charge.

S2. A microfabricated variable capacitor, comprising:
a stator (X40) having a width and including a plurality of electrically conductive plates each spaced apart from one another, each said pair of adjacent plates forming a channel, each of said plates being in a first common electrical communication;
a rotor (X60) having a length and including a plurality of electrically conductive blades, said rotor being suspended relative to said stator such that each of said blades is received within a corresponding one of said channels and each said blade overlaps with an area of an adjacent said plate, each of said blades being in a second common electrical communication; and
a suspension system (70) for flexibly coupling said rotor relative to said stator, said system flexibly coupling to said stator at a location about midway across the width, said system flexibly coupling to said rotor at a location about midway along the length.

S3. A method for transducing air pressure, comprising:
providing a flexible diaphragm (X80), a stator (X40) including a plurality of electrically conductive plates, and a rotor (X60) movable relative to the stator and including a plurality of electrically conductive blades;
interdigitating the blades and the plates;
coupling the diaphragm to the rotor such that the motion of the rotor is responsive to movement of a portion of the diaphragm in one direction;
applying a pressure differential across the diaphragm;
deflecting the diaphragm by said applying;
moving the blades (X64) relative to the plates (X44) by said deflecting; and
changing the electrical capacitance by said moving.

Any of the statements above, which further comprises a flexible diaphragm having a shape responsive to a pressure, and a distended shape of said diaphragm coacts with said springs to change the position of said rotor relative to said stator; which further comprises a member for coupling the motion of said diaphragm to the motion of said hub; wherein said member has two ends, one end being in contact with said diaphragm and the other end being in contact with said hub; wherein said member is integral with one of said diaphragm or said hub; or wherein said member is not integral with the other of said diaphragm or said hub.

Any of the statements above, which further comprises means for varying the position of said rotor relative to said stator; wherein said means includes a flexible diaphragm the shape of which is responsive to ambient pressure, and the motion of said diaphragm changes the position of said rotor relative to said stator; wherein said diaphragm is responsive to sound; wherein said diaphragm is part of a voice transducer for a cell phone; wherein said means includes coupling said capacitor to a moving object, and the relative motion is related to the inertia of said rotor; wherein said capacitor is part of an accelerometer; wherein said means includes a flexible object, said stator is coupled to one portion of the object, said rotor is coupled to another portion of the object, and the one portion moves relative to the other portion; or wherein said capacitor is part of a strain measuring system.

Any of the statements above wherein said suspension system includes a first cantilever support extending from one end of said stator to said rotor and a second cantilever support extending from the opposite end of said stator to said rotor; or wherein said first cantilever extends from the one end with approximately clamped boundary conditions and said second cantilever extends from the other end with approximately clamped boundary conditions.

Any of the statements above wherein said suspension system couples to said rotor such that such said rotor is mass balanced in two dimensions relative to said stator; wherein said rotor includes a centrally located hub, and said blades are cantileveredly supported from said hub; which further comprises a cantilever arm supporting said blades, one end of said arm being coupled to said hub, each said blade extending from said arm in a direction that is generally transverse to the direction from the hub to the free end of said arm; wherein said plates are planar and said blades are planar; or wherein said plates are circular about an axis and said blades are circular about the same axis.

Any of the statements above wherein said moving is by translating the blades between the plates; which further comprises suspending the rotor from the middle of the stator; wherein said suspending is to the middle of the rotor; or wherein said coupling is to the middle of the rotor.

Any of the statements above wherein said coupling is between the middle of the rotor and the middle of the diaphragm; wherein said coupling approximates a point load on the rotor; or which further comprises microfabricating the rotor, the stator, and the diaphragm.

Any of the statements above wherein said coupling includes that the diaphragm cannot substantially apply a moment to the rotor; wherein the diaphragm is substantially planar and the one direction is generally normal to the plane; or wherein said coupling includes the diaphragm displacing the rotor relative to the stator before said applying.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

The invention claimed is:

1. A microfabricated variable capacitor, comprising:
a stator including a plurality of electrically conductive plates each spaced apart from one another, each pair of adjacent plates forming a channel therebetween, each of said plates being in a first common electrical communication; and
a rotor including a central hub and first and second arms extending in cantilever manner from opposite sides of said hub, a first plurality of electrically conductive blades being coupled to said first arm and a second plurality of electrically conductive blades being coupled to said second arm, each of said first plurality and said second plurality of blades being in a second common electrical communication;
wherein said central hub is suspended from said stator by first and second springs, such that each of said blades is received within a corresponding one of said channels and a portion of each said blade coacts with an adjacent said plate to store electrical charge, and the capacitance between the first electrical communication and the second electrical communication varies as said first and second springs bias the rotor and the central hub to different vertical positions relative to said stator.

2. The capacitor of claim 1 which further comprises a flexible diaphragm having a shape responsive to a pressure, and a distended shape of said diaphragm coacts with said springs to change the vertical position of said rotor relative to said stator.

3. The capacitor of claim 2 which further comprises a member for coupling the motion of said diaphragm to the vertical motion of said hub.

4. The capacitor of claim 3 wherein said member has two ends, one end being in contact with said diaphragm and the other end being in contact with said hub.

5. The capacitor of claim 3 wherein said member is integral with one of said diaphragm or said hub.

6. The capacitor of claim 3 wherein said member is not integral with the other of said diaphragm or said hub.

7. The capacitor of claim 1 which further comprises means for varying the vertical position of said rotor relative to said stator.

8. The capacitor of claim 7 wherein said means includes a flexible diaphragm the shape of which is responsive to ambient pressure, and the motion of said diaphragm changes the position of said rotor relative to said stator.

9. The capacitor of claim 8 wherein said diaphragm is responsive to sound.

10. The capacitor of claim 8 wherein said diaphragm is part of a voice transducer for a cell phone.

11. The capacitor of claim 7 wherein said means for varying the vertical position of said rotor relative to said stator includes coupling said capacitor to a moving object, and said varying of the vertical position of said rotor relative to said stator is related to the inertia of said rotor.

12. The capacitor of claim 11 wherein said capacitor is part of an accelerometer.

13. The capacitor of claim 7 wherein said means includes a flexible object, said stator is coupled to one portion of the object, said rotor is coupled to another portion of the object, and the one portion moves relative to the other portion.

14. The capacitor of claim 13 wherein said capacitor is part of a strain measuring system.

15. The capacitor of claim 1 wherein each said first and second spring have a first spring constant corresponding to vertical movement of said blades parallel to said plates, and a second spring constant corresponding to movement of said blades toward said plates, and the second spring constant is greater than the first spring constant.

16. The capacitor of claim 8 wherein said diaphragm, said rotor, and said stator are adapted and configured to be implanted in the lung of an animal.

17. A method for transducing air pressure, comprising:
providing a flexible diaphragm, a stator including a plurality of electrically conductive plates, and a rotor movable relative to the stator and including a pair of parallel support arms and a first plurality of electrically conductive blades extending laterally outward from one support arm and a second plurality of electrically conductive blades extending laterally outward from the other support arm;
interdigitating the blades and the plates;
coupling the diaphragm to the rotor such that the motion of the rotor is responsive to movement of a portion of the diaphragm in one direction and substantially unresponsive to movement of the portion of the diaphragm in any direction orthogonal to the one direction;
applying a pressure differential across the diaphragm;
deflecting the diaphragm by said applying;
moving the first and second plurality of blades relative to the plates by said deflecting; and
changing the electrical capacitance of the rotor and stator by said moving.

18. The method of claim 17 wherein said moving is by translating the blades between the plates.

19. The method of claim 17 which further comprises suspending the rotor from the middle of the stator.

20. The method of claim 19 which further comprises suspending the rotor from the middle of the rotor.

21. The method of claim 20 wherein said coupling is to the middle of the rotor.

22. The method of claim 17 wherein said coupling is between the middle of the rotor and the middle of the diaphragm, and said coupling does not include attaching the diaphragm to the rotor.

23. The method of claim 17 wherein said coupling approximates a point load on the rotor.

24. The method of claim 17 which further comprises microfabricating the rotor, the stator, and the diaphragm.

25. The method of claim 17 wherein said coupling does not substantially apply a moment to the rotor.

26. The method of claim 17 wherein the diaphragm is substantially planar and the one direction is generally normal to the plane.

27. The method of claim 17 wherein said coupling includes the diaphragm displacing the rotor relative to the stator before said applying.

28. The capacitor of claim 16 wherein ambient pressure is intrapleural pressure.

29. The capacitor of claim 17 wherein said diaphragm, said rotor, and said stator are adapted and configured to be implanted in an animal, and which further comprises implanting the capacitor in the airway of an animal.

30. The capacitor of claim 29 wherein the applied pressure differential includes intrapleural pressure.

\* \* \* \* \*